(12) United States Patent
Nakai et al.

(10) Patent No.: US 11,419,486 B2
(45) Date of Patent: Aug. 23, 2022

(54) ENDOSCOPE INCLUDING THE OPERATION MECHANISM

(71) Applicant: Olympus Corporation, Hachioji (JP)

(72) Inventors: Yuta Nakai, Aizuwakamatsu (JP); Reiji Koyama, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 355 days.

(21) Appl. No.: 16/674,066

(22) Filed: Nov. 5, 2019

(65) Prior Publication Data

US 2020/0069150 A1 Mar. 5, 2020

Related U.S. Application Data

(63) Continuation of application No. PCT/JP2018/007334, filed on Feb. 27, 2018.

(30) Foreign Application Priority Data

May 9, 2017 (JP) .............................. JP2017-093101
May 9, 2017 (JP) .............................. JP2017-093102

(51) Int. Cl.
  *A61B 1/005* (2006.01)
  *A61B 17/00* (2006.01)

(52) U.S. Cl.
  CPC .......... *A61B 1/0052* (2013.01); *A61B 1/0057* (2013.01); *A61B 2017/00367* (2013.01)

(58) Field of Classification Search
  CPC ................ A61B 1/0052; A61B 1/0057; A61B 2017/00367
  See application file for complete search history.

(56) References Cited

U.S. PATENT DOCUMENTS

| 2001/0037051 A1* | 11/2001 | Fujii | .............. A61B 1/0052 600/146 |
| 2014/0058323 A1* | 2/2014 | Hoshino | .......... A61M 25/0147 604/95.04 |
| 2014/0296640 A1 | 10/2014 | Hoshino | |

FOREIGN PATENT DOCUMENTS

| JP | 2004313806 | 11/2004 |
| JP | 5629039 | 9/2016 |

(Continued)

OTHER PUBLICATIONS

International Search Report and Written Opinion from corresponding International Application No. PCT/JP2018/007334, dated May 29, 2018.

*Primary Examiner* — Alexandra L Newton
*Assistant Examiner* — Rynae E Boler
(74) *Attorney, Agent, or Firm* — Oliff PLC

(57) ABSTRACT

The disclosed technology is directed to an endoscope having respective first and second operations, a movable member, respective support and friction members, a cam member and a click mechanism all of which are engaged with one another to operate the endoscope during an operation. First and second operation members are disposed in the endoscope and are rotationally operated around a predetermined axis to carry out operation of the endoscope. A movable member is disposed inside the first operation member and is movable between a first position and a second position. A cam member having a cam surface that is made with an inclination with respect to the predetermined axis and abuts against part of the movable member. A click mechanism holds the cam member at the first position or the second position.

10 Claims, 9 Drawing Sheets

(56) References Cited

FOREIGN PATENT DOCUMENTS

| WO | 2013061690 | 5/2013 |
| WO | 2014065093 | 5/2014 |

\* cited by examiner

ENDOSCOPE INCLUDING THE OPERATION MECHANISM

CROSS-REFERENCE TO RELATED APPLICATIONS

This application is a continuation application of PCT Application No. PCT/JP2018/007334 filed on Feb. 27, 2018, which in turn claim priority to the Japanese Patent Application No. 2017-093101 filed on May 9, 2017 in Japan and Japanese Patent Application No. 2017-093102 filed on May 9, 2017, which are hereby incorporated by reference in its entirety.

TECHNICAL FIELD

This disclosed technology relates to an operation mechanism of an endoscope that is disposed in an operation portion of the endoscope and is for carrying out bending operation of a bending portion of an insertion portion of the endoscope and an endoscope including this operation mechanism of the endoscope.

DESCRIPTION OF THE RELATED ART

Conventional endoscope is configured to have an engagement mechanism including operation members, or lever, knob, and so forth, for fixing the operation position of the multiple bending operation knobs and keeping the desired bending angle of the bending portion when rotation operation of each of the multiple bending operation knobs is carried out and the bending portion is bent.

For example, an operation mechanism of an endoscope disclosed by Japanese U.S. Pat. No. 5,629,039 and so forth has multiple bending operation knobs, or upward-downward bending operation knob and left-right bending operation knob, and an engagement mechanism configured with an engagement cam, a movable disc, and a friction member is disclosed.

The engagement mechanism is configured to include a click mechanism that generates a feeling of click to notify an operator of on/off-switching of the engagement state.

Furthermore, by rotating the engagement cam around an axis by using an engagement operation member, the movable disc is moved in the axial direction by action of an inclination of this engagement cam. Along with this, the friction member disposed between the movable disc and a support portion is compressed in the axial direction and is deformed. Thereby, the friction member gives a friction load in the rotation direction to the bending operation knob. Therefore, this friction member regulates the rotation of the bending operation knob.

In this case, the engagement operation member is rotationally operated for on/off-switching of the engagement state. It is desirable that the amount of rotation operation force, or rotation torque, at the time of engagement-on/off operation of the engagement operation member at this time is set as small as possible in terms of operability of the endoscope.

On the other hand, in recent years, there has been a demand for a higher engagement holding force in the operation mechanism of the endoscope, particularly in the bending operation mechanism.

However, in order to enhance the engagement holding force without changing the configuration of the operation mechanism of the conventional endoscope disclosed in Japanese Patent No. 5629039 described hereinbefore and so forth, for example, a configuration in which the reaction force of a click spring in the click mechanism is set high and a configuration in which the pressurizing force to the friction member by the engagement cam is set high is employed. However, with only such a configuration, a problem that the feeling of click generated at the time of on/off-switching of the engagement state is weakened arises.

Moreover, as means to suppress the amount of rotation operation force, or rotation torque, at the time of engagement on/off-switching operation of the engagement operation member to a small amount without changing the configuration of the operation mechanism of the conventional endoscope disclosed in Japanese Patent No. 5629039 described hereinbefore and so forth, for example, a countermeasure of making the configuration to cause the rotation angle of the engagement cam to become large is conceivable.

Here, it is known that the inclination angle of the engagement cam can be made gentler when the rotation angle of the engagement cam is larger. Furthermore, when the inclination angle of the engagement cam is gentler, the amount of rotation operation force, or rotation torque, at the time of engagement on/off-switching operation of the engagement operation member can be suppressed to a smaller amount.

However, when the configuration is made to merely cause the rotation angle of the engagement cam to become large, the rotation angle of the engagement operation member necessary at the time of engagement on/off-switching operation also becomes large. Thus, a problem that operability of the endoscope is impaired arises.

Therefore, in the engagement mechanism applied to the operation mechanism of the endoscope, the rotation angle of the engagement operation member at the time of engagement on/off-switching operation needs to be limited to fall within a predetermined range in which operability of the endoscope is not impaired.

Therefore, there is a need for operation mechanisms of endoscopes, particularly in operation mechanisms with which bending operation of a bending portion are carried out such that can implement causing a feeling of click by a click mechanism for sensing on/off-switching of an engagement state to become clear without impairing operability of the endoscope.

BRIEF SUMMARY OF EMBODIMENTS

One aspect of the disclosed technology is directed to an endoscope having respective first and second operations, a movable member, respective support and friction members, a cam member and a click mechanism all of which are engaged with one another to operate the endoscope during an operation. A first operation member is disposed in the endoscope and is rotationally operated around a predetermined axis to carry out operation of the endoscope. A second operation member is disposed in the endoscope and is rotationally operated around the predetermined axis to carry out rotation regulation of the first operation member. A movable member is disposed inside the first operation member and is movable between a first position at which the movable member permits rotation of the first operation member and a second position at which the movable member regulates rotation of the first operation member through separation from the first position in a direction along the predetermined axis. A support member is disposed with intermediary of a predetermined interval with respect to the movable member in the direction along the predetermined axis. A friction member that is disposed between the support member and the movable member and is compressed and deformed between the support member and the movable member when the movable member moves from the first position to the second position so as to give a friction force to the rotation of the first operation member and to regulate the rotation of the first operation member. A cam member having a cam surface that is made with an inclination with respect to the predetermined axis and abuts against part of the movable member. The cam member receives operation input from external through the second operation member and moves the movable member between the first position and the second position. A click mechanism holds the cam member at the first position or the second position in which an amount of movement of the movable member in the direction along the predetermined axis by the cam surface changes to become gentler in middle of compression of the friction member by the movable member.

Another aspect of the disclosed technology is directed to an endoscope having an endoscope having respective first and second operations, a movable member, respective support and friction members, a cam member and a biasing member all of which engaged with one another to operate the endoscope during an operation. A first operation member is disposed in the endoscope and is rotationally operated around a predetermined axis to carry out operation of the endoscope. A second operation member that is disposed in the endoscope and is rotationally operated around the predetermined axis to carry out rotation regulation of the first operation member. A movable member is disposed inside the first operation member and is movable between a first position at which the movable member permits rotation of the first operation member and a second position at which the movable member regulates rotation of the first operation member through separation from the first position in a direction along the predetermined axis. A support member is disposed with intermediary of a predetermined interval with respect to the movable member in the direction along the predetermined axis. A friction member is disposed between the support member and the movable member and is compressed and deformed between the support member and the movable member when the movable member moves from the first position to the second position so as to give a friction force to the rotation of the first operation member and to regulate the rotation of the first operation member. A cam member having a cam surface is made with an inclination with respect to the predetermined axis and abuts against part of the movable member. The cam member receives operation input from external through the second operation member and moves the movable member between the first position and the second position. A biasing member that biases the movable member toward the first position in which an amount of movement of the movable member in the direction along the predetermined axis by the cam surface changes to become gentler after the movable member has started compression of the friction member.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

Figure 1:
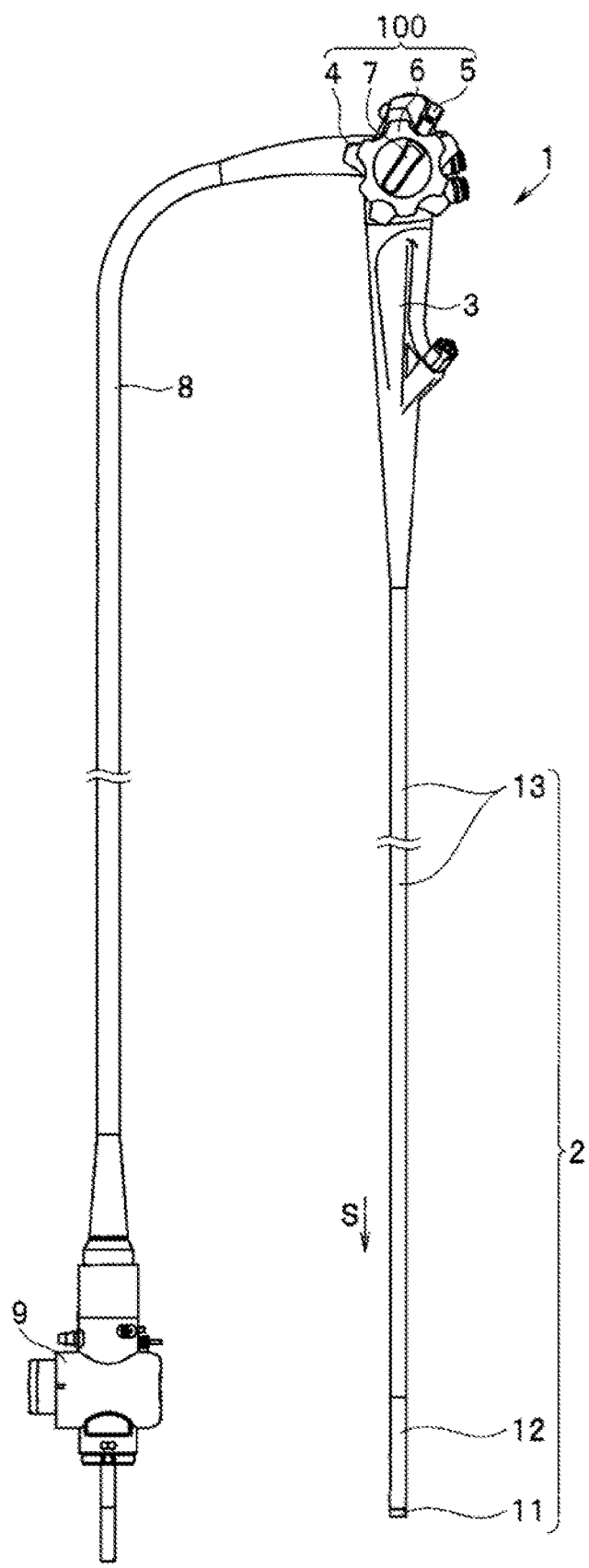
FIG. 1 is an appearance diagram illustrating the overall configuration of an endoscope including an operation mechanism of an endoscope in a first embodiment of the disclosed technology.

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

The disclosed technology will be described hereinafter based on diagrammatically-represented embodiments. Each drawing used for the following description is what is schematically illustrated, and the dimensional relationship, scale, and so forth of the respective members are illustrated in such a manner as to be made different for each constituent element in some cases in order to illustrate each constituent element with such a size as to be recognizable on the drawings. Therefore, the disclosed technology is not limited to only diagrammatically-represented forms regarding the quantity of each constituent element depicted in the respective drawings, the shape of each constituent element, the ratio of the sizes of the respective constituent elements, the relative positional relationship of the respective constituent elements, and so forth.

The disclosed technology is made in view of the points described hereinbefore and an object thereof is to provide, in operation mechanisms of endoscopes, particularly in operation mechanisms with which bending operation and so forth of a bending portion of an insertion portion are carried out, an operation mechanism of an endoscope having a configuration that can implement causing a feeling of click by a click mechanism for sensing on/off-switching of an engagement state to become clear without impairing operability of the endoscope and even when a configuration to enhance the engagement holding force is employed.

Furthermore, another object of the disclosed technology is to provide, in operation mechanisms of endoscopes, particularly in operation mechanisms with which bending operation and so forth of a bending portion of an insertion portion are carried out, an operation mechanism of an endoscope that can ensure the necessary engagement holding force without impairing operability of the endoscope while suppressing the rotation angle of an engagement operation member within a predetermined range, and an endoscope including this operation mechanism of an endoscope.

According to the disclosed technology, it is possible to provide, in operation mechanisms of endoscopes, particularly in operation mechanisms with which bending operation and so forth of a bending portion of an insertion portion are carried out, an operation mechanism of an endoscope having a configuration that can implement causing a feeling of click by the click mechanism for sensing on/off-switching of the engagement state to become clear without impairing operability of the endoscope and even when a configuration to enhance the engagement holding force is employed.

Furthermore, according to the disclosed technology, it is possible to provide, in operation mechanisms of endoscopes, particularly in operation mechanisms with which bending operation and so forth of a bending portion of an insertion portion are carried out, an operation mechanism of an endoscope that can ensure the necessary engagement holding force without impairing operability of the endoscope while suppressing the rotation angle of the engagement operation member within a predetermined range, and an endoscope including this operation mechanism of an endoscope.

Each embodiment to be described hereinafter exemplifies a bending operation mechanism for carrying out bending operation of a bending portion of an insertion portion of an endoscope as one example of an operation mechanism of an endoscope.

First Embodiment

FIG. 1 to FIG. 7 are diagrams illustrating a first embodiment of the disclosed technology. Among them, FIG. 1 is an appearance diagram illustrating the overall configuration of an endoscope including an operation mechanism of an endoscope in the first embodiment of the disclosed technology.

First, the overall configuration of the endoscope including the operation mechanism of an endoscope in the first embodiment of the disclosed technology will be simply described hereinafter by using FIG. 1.

As illustrated in FIG. 1, an endoscope 1 is mainly configured to include an insertion portion 2 inserted into a test subject, an operation portion 3 disposed continuously with the proximal side of the insertion portion 2 in an insertion direction (direction of an arrow S in FIG. 1), a universal cord 8 extended from the operation portion 3, a connector 9 disposed on the distal side of the universal cord 8, and so forth.

The endoscope 1 configures an endoscope system as a whole by being electrically connected to external apparatuses such as a control apparatus and an illuminating apparatus, which are not illustrated in the diagram, through the connector 9.

The insertion portion 2 is composed of a distal portion 11, a bending portion 12, and a flexible tube portion 13 that are continuously disposed sequentially from the distal side. The insertion portion 2 is formed into an elongated tube shape along the insertion direction S.

Inside the distal portion 11, an imaging unit for observing the inside of the test subject, an illuminating unit for illuminating the inside of the test subject, and so forth are disposed (neither is illustrated in the diagram). The bending portion 12 is disposed continuously with the proximal side of the distal portion 11.

Although detailed diagrammatic representation is omitted, the bending portion 12 is a constituent part configured through joining of multiple bending pieces along the insertion direction S of the insertion portion 2, for example. The bending portion 12 freely bends in four directions of upward, downward, left, and right directions through a bending operation mechanism 100 (to be described in detail hereinafter) disposed inside the operation portion 3 in response to forward/reverse rotation operation of operation members (bending operation knobs 4 and 6 to be described hereinafter) disposed in the operation portion 3.

Furthermore, through upward, downward, leftward, and rightward bending of the bending portion 12, the bending portion 12 is used for varying the observation direction of the imaging unit of the distal portion 11 and improving the insertability of the distal portion 11 in the test subject. The flexible tube portion 13 is disposed continuously with the proximal side of the bending portion 12.

The flexible tube portion 13 is an elongated tubular member that joins the bending portion 12 and the operation portion 3. Inside the flexible tube portion 13, bending operation wires, communication line and power feed line to the imaging unit, an optical fiber to the illuminating unit, and so forth are inserted and disposed although diagrammatic representation is omitted. The operation portion 3 is disposed continuously with the proximal side of the flexible tube portion 13.

The operation portion 3 is configured to internally have the bending operation mechanism 100 for bending the bending portion 12 of the insertion portion 2 in upward, downward, left, and right directions. In the bending operation mechanism 100, multiple bending operation members (see numeral references 4 and 6) disposed on the outer surface of the operation portion 3 are included.

Specifically, as the multiple bending operation members, there are the upward-downward bending operation knob 4 operated when bending operation in the upward-downward direction is carried out and the left-right bending operation knob 6 operated when bending operation in the left-right direction is carried out, for example. Here, the upward-downward bending operation knob 4 and the left-right bending operation knob 6 are rotating knobs for causing the bending portion 12 in the endoscope 1 to work.

Figure 2:
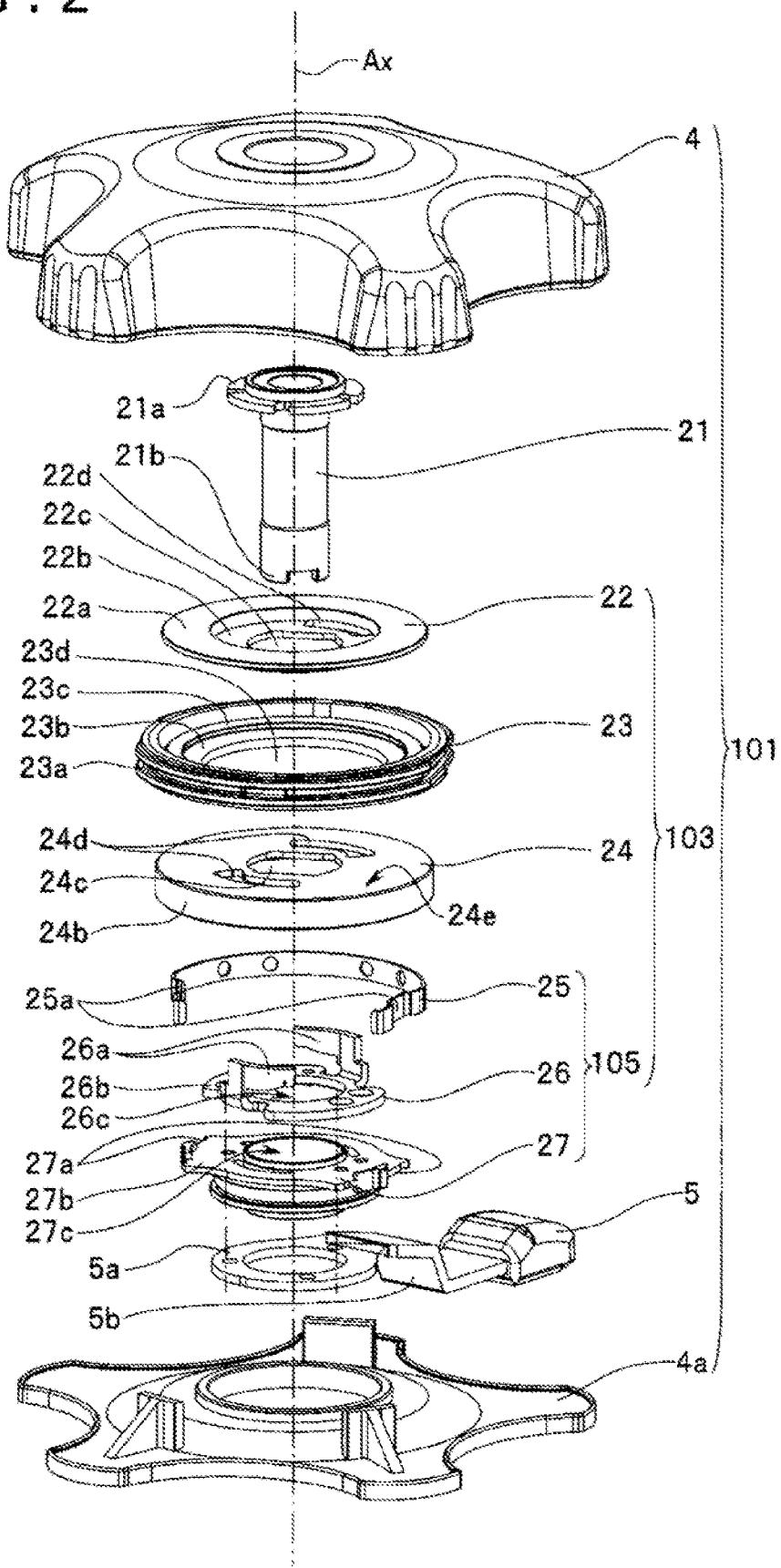
FIG. 2 is a main-part enlarged exploded perspective view illustrating the configuration of an upward-downward direction bending operation mechanism in the operation mechanism of an endoscope in the first embodiment of the disclosed technology.

That is, these upward-downward bending operation knob 4 and left-right bending operation knob 6 are operation members that are disposed in the endoscope 1 and with which bending operation of the endoscope 1 is carried out by rotation operation in the forward/reverse direction around a predetermined axis (see a rotation center axis Ax in FIG. 2). These upward-downward bending operation knob 4 and left-right bending operation knob 6 will be referred to as first operation members.

Furthermore, in the bending operation mechanism 100, multiple engagement operation members (5 and 7) for fixing the rotation position of the respective bending operation knobs (4 and 6) and keeping the desired bending angle of the bending portion 12 and engagement mechanisms (103 and 104; not illustrated in FIG. 1; details will be described hereinafter) that act in conjunction with these multiple engagement operation members (5 and 7) are included.

As the multiple engagement operation members (5 and 7), specifically, there are the engagement lever 5 and the engagement knob 7, for example. The engagement lever is an operation member operated when the rotation position of the upward-downward bending operation knob 4 is attached and the desired bending angle of the bending portion 12 in the upward-downward direction is kept or when the fixed-kept state is canceled. The engagement knob 7 is an operation member operated when the rotation position of the left-right bending operation knob 6 is attached and the desired bending angle of the bending portion 12 in the left-right direction is kept or when the fixed-kept state is canceled.

That is, these engagement lever 5 and engagement knob 7 are operation members that are disposed in the endoscope 1 and with which rotation regulation of the respective bending operation knobs (4 and 6; first operation members) is carried out by rotation operation in the forward/reverse direction around the predetermined axis (see a rotation center axis Ax in FIG. 2). These engagement lever 5 and engagement knob 7 will be referred to as second operation members.

Supposing that the other configuration in the endoscope 1 described hereinbefore is substantially the same as the conventional endoscope, detailed description thereof is omitted.

Next, the bending operation mechanism 100 that is the operation mechanism of an endoscope in the present embodiment and is included in the endoscope 1 will be described hereinafter by using FIG. 2 to FIG. 7.

Figure 3:
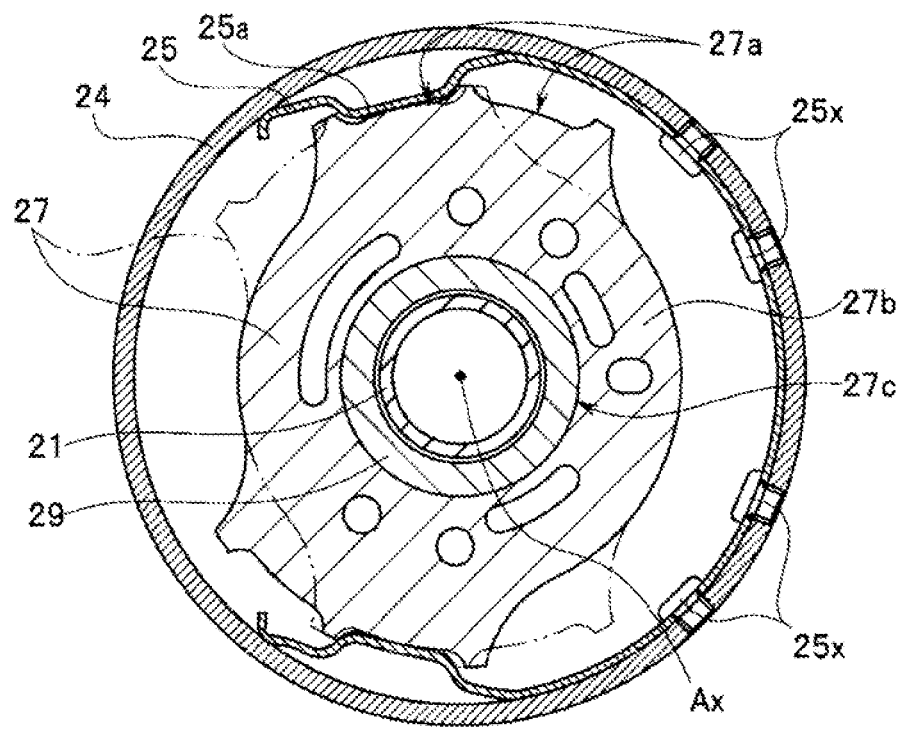
FIG. 3 is a main-part enlarged sectional view mainly illustrating the configuration of a click mechanism in the upward-downward direction bending operation mechanism in FIG. 2.
Figure 4:
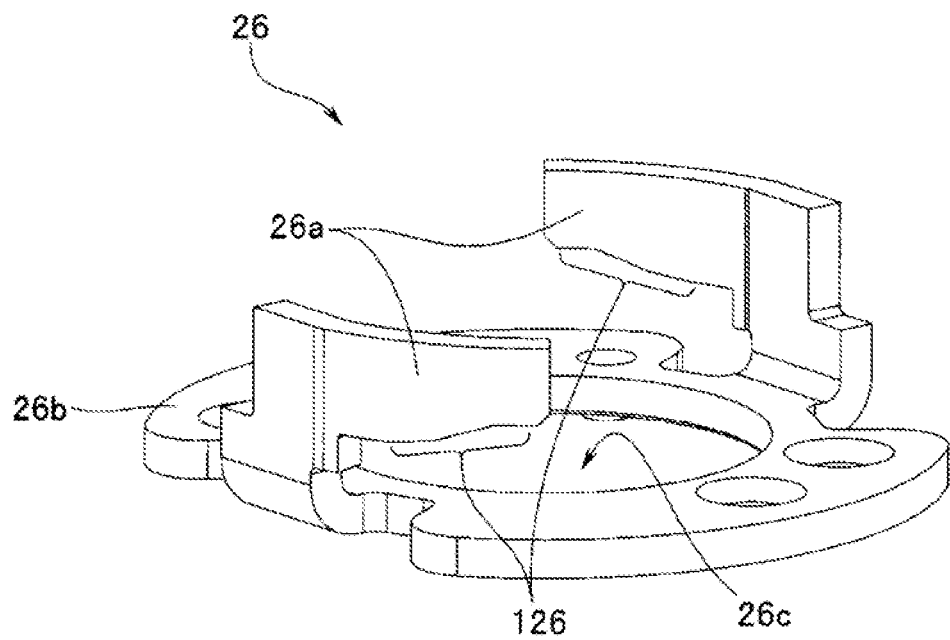
FIG. 4 is a main-part enlarged perspective view in which only an engagement cam member in the constituent members configuring the upward-downward direction bending operation mechanism in FIG. 2 is extracted and illustrated.
Figure 5:
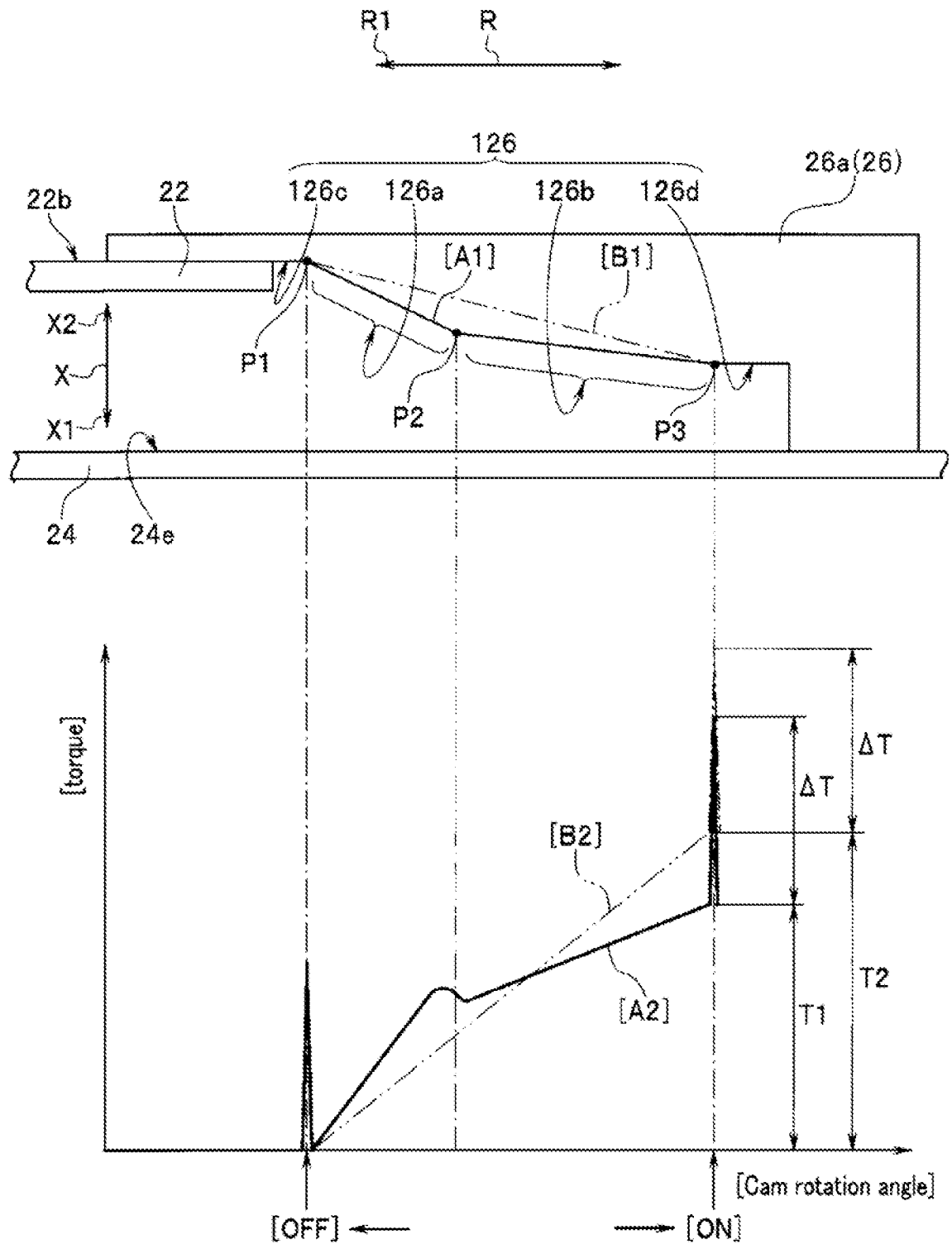
FIG. 5 is a diagram that conceptually illustrates an engagement mechanism in the upward-downward direction bending operation mechanism in FIG. 2 and specifically illustrates the shape a cam surface of the engagement cam member and in which the relationship between the rotation angle of the engagement cam member, or operation member, and the engagement torque generated by the engagement mechanism according to this is turned to a graph and is illustrated.

FIG. 2 is a main-part enlarged exploded perspective view illustrating the configuration of an upward-downward direction bending operation mechanism in the operation mechanism of an endoscope in the first embodiment of the disclosed technology. FIG. 3 is a main-part enlarged sectional view mainly illustrating the configuration of a click mechanism in the upward-downward direction bending operation mechanism in FIG. 2. In FIG. 3, action when a click cam plate rotates is simultaneously illustrated (see a two-dot chain line). FIG. 4 is a main-part enlarged perspective view in which only an engagement cam member in the constituent members configuring the upward-downward direction bending operation mechanism in FIG. 2 is extracted and illustrated. FIG. 5 is a diagram that conceptually illustrates the engagement mechanism and specifically illustrates the shape a cam surface of the engagement cam member in FIG. 4 and in which the relationship between the rotation angle of the engagement cam member, or operation member, and the engagement torque generated by the engagement mechanism according to this is turned to a graph and is illustrated.

Figure 6:
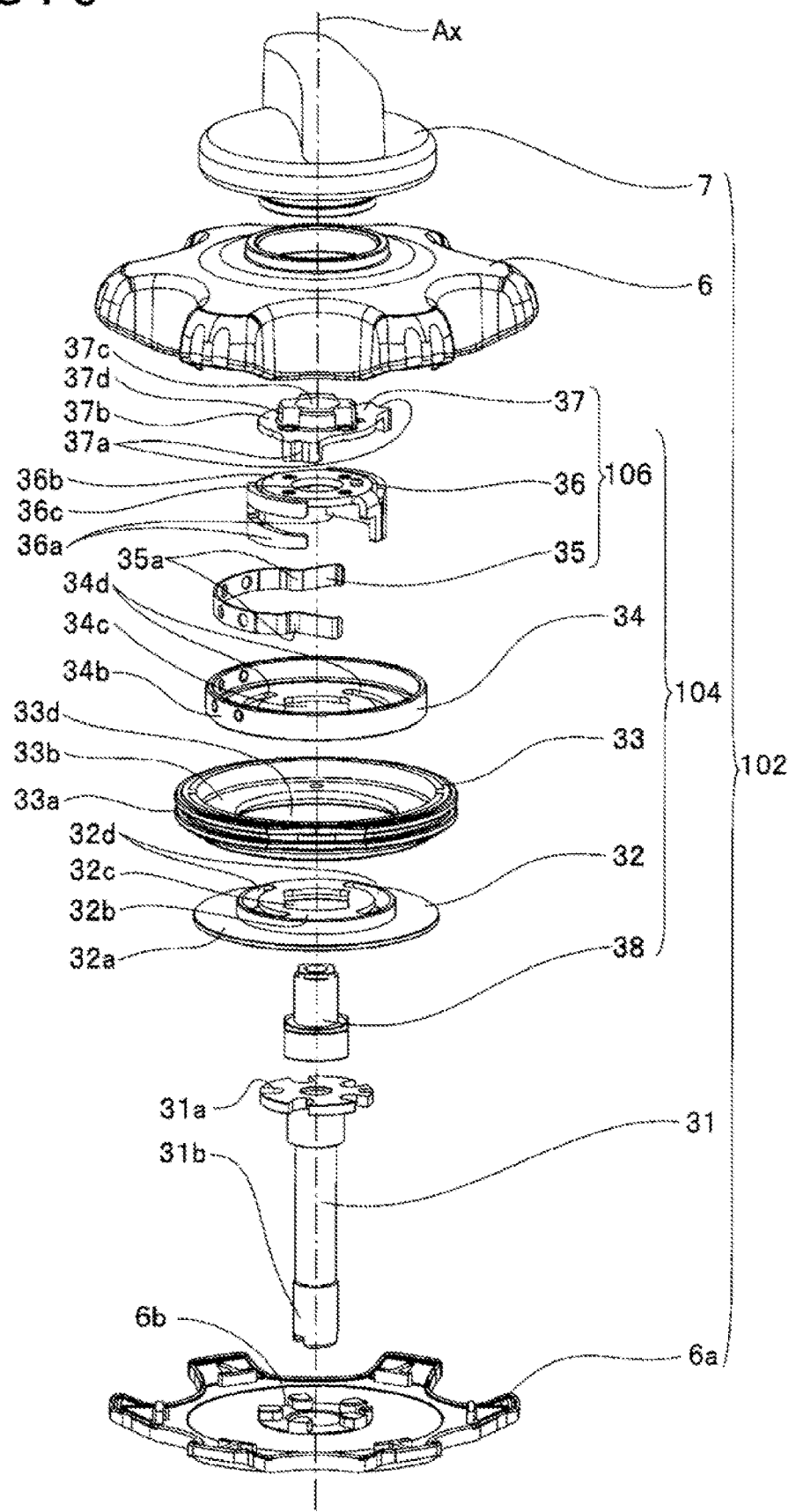
FIG. 6 is a main-part enlarged exploded perspective view illustrating the configuration of a left-right direction bending operation mechanism in the operation mechanism of an endoscope in the first embodiment of the disclosed technology.
Figure 7:
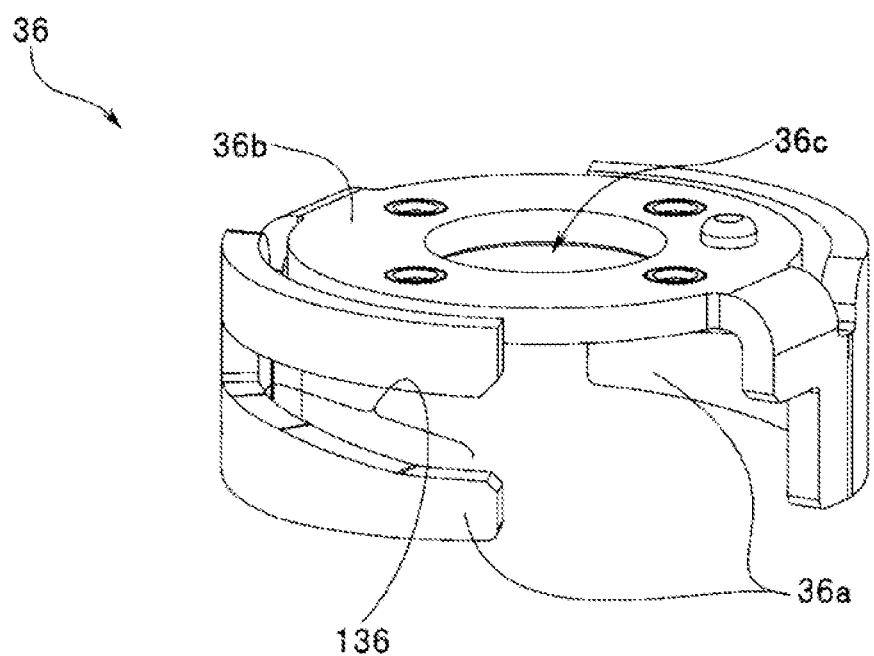
FIG. 7 is a main-part enlarged perspective view in which only an engagement cam member in the constituent members configuring the left-right direction bending operation mechanism in FIG. 6 is extracted and illustrated.

Furthermore, FIG. 6 is a main-part enlarged exploded perspective view illustrating the configuration of a left-right direction bending operation mechanism in the operation mechanism of an endoscope in the first embodiment of the disclosed technology. FIG. 7 is a main-part enlarged perspective view in which only an engagement cam member in the constituent members configuring the left-right direction bending operation mechanism in FIG. 6 is extracted and illustrated.

The bending operation mechanism 100 of the endoscope 1 (see FIG. 1) of the present embodiment is composed of an upward-downward direction bending operation mechanism 101 (see FIG. 2) for bending the bending portion 12 of the insertion portion 2 of the endoscope 1 in the upward-downward direction and a left-right direction bending operation mechanism 102 (see FIG. 6) for bending the bending portion 12 in the left-right direction.

As illustrated in FIG. 2, the upward-downward direction bending operation mechanism 101 is composed mainly of the upward-downward bending operation knob 4, an upward-downward bending operation knob lower cover 4a, a rotating shaft 21, the engagement lever 5, the engagement mechanism 103, and so forth.

The upward-downward bending operation knob 4 is an operation member operated by an operator when bending operation in the upward-downward direction is carried out. The upward-downward bending operation knob 4 in the present embodiment is exemplified as an operation member of a rotation system.

The upward-downward bending operation knob lower cover 4a is a cover member that covers the lower surface side of the upward-downward bending operation knob 4. Here, when the upward-downward bending operation knob 4 and the upward-downward bending operation knob lower cover 4a are mated, a space of a predetermined region is formed between both. In this space, each constituent component of the upward-downward direction bending operation mechanism 101 including the engagement mechanism 103 is disposed.

The rotating shaft 21 is a power transmitting member for transmitting rotation of the upward-downward bending operation knob 4 to a sprocket or pulley (they are also constituent members of the upward-downward direction bending operation mechanism 101 but are not illustrated) disposed inside the operation portion 3 and rotating the sprocket or pulley.

For this purpose, one end of the rotating shaft 21 is joined to the upward-downward bending operation knob 4 whereas the other end penetrates the outer wall surface of the operation portion 3 and is disposed to protrude in the internal space thereof. In this case, the rotating shaft 21 is inserted and disposed in such a manner as to be capable of free forward/reverse rotation inside a fixing shaft 29 (not illustrated in FIG. 2; see FIG. 3) that extends from the inside of the operation portion 3 and has a cylindrical shape. The rotating shaft 21 and the fixing shaft 29 (see FIG. 3) are disposed along a direction substantially orthogonal to the insertion direction S of the insertion portion 2.

An engaging portion 21a is formed at one end of the rotating shaft 21. The engaging portion 21a engages with multiple engaged projected portions (not illustrated) formed around the rotation center axis Ax (see one-dot chain line in FIG. 2) of the upward-downward bending operation knob 4 on the inner surface side of the knob 4. Due to this, the configuration is made in such a manner that, when the upward-downward bending operation knob 4 is rotated around the rotation center axis Ax, the rotating shaft 21 also rotates in the same direction in conjunction with the upward-downward bending operation knob 4.

The rotating shaft 21 penetrates the engagement mechanism 103 inside the upward-downward bending operation knob 4 and penetrates the relevant upward-downward bending operation knob lower cover 4a to be disposed to protrude to the inside of the operation portion 3.

Furthermore, the other end 21b of the rotating shaft 21 is fitted to the rotation center of the sprocket or pulley, or part of the upward-downward direction bending operation mechanism 101, which is not illustrated, inside the operation portion 3. Supposing that, in the upward-downward direction bending operation mechanism 101, the configuration subsequent to the sprocket or pulley is the same as the bending mechanism in the conventional general endoscope, diagrammatic representation and description thereof are omitted.

The engagement lever 5 is an operation member that acts on the engagement mechanism 103. As described hereinbefore, the engagement lever 5 is an operation member for switching operation between an engagement state, or engagement-on, in which the rotation position of the upward-downward bending operation knob 4 is attached and the desired bending angle of the bending portion 12 in the upward-downward direction is kept and an engagement free state (hereinafter, abbreviated as free state, or engagement-off) in which bending operation can be freely carried out through canceling of the fixed-kept state of this engagement state, or engagement-on.

As the engagement lever 5 in the present embodiment, an operation member with a lever shape is exemplified. The engagement lever 5 is formed to have a circular ring portion 5a to which a click cam plate 27 is attached and an operation portion 5b disposed to protrude in the radial direction from part of the outer circumferential edge of the circular ring portion 5a.

The engagement lever 5 is disposed in such a manner as to be capable of free forward/reverse rotation in a predetermined range around the rotation center axis Ax of the upward-downward bending operation knob 4. This allows the operator to carry out on/off-switching of the engagement state of the upward-downward bending operation knob 4, i.e., switch the engagement state and the free state, by making forward/reverse rotation of the engagement lever 5 in the predetermined range around the rotation center axis Ax of the upward-downward bending operation knob 4.

The engagement mechanism 103 is a mechanism portion that receives operation input of the engagement lever 5 and implements the engagement state and the free state of the upward-downward bending operation knob 4.

The engagement mechanism 103 is composed mainly of a movable circular plate 22, a friction member 23, a support member 24, an engagement cam member 26, a click mechanism 105 including a click spring 25, the click cam plate 27, and so forth.

The movable circular plate 22, which will be described in detail hereinafter, is disposed inside the upward-downward bending operation knob 4, or first operation member. The movable circular plate 22 is a movable member that receives action of engagement cam portions 26a of the engagement cam member 26 to be described hereinafter and can move between a position, or referred to as first position, at which the movable circular plate 22 permits rotation of the upward-downward bending operation knob 4, or first operation member, and a position, or referred to as second position, at which the movable circular plate 22 regulates rotation of the upward-downward bending operation knob 4, or first operation member, through separation from this first position in the direction along the rotation center axis Ax, or predetermined axis. Here, the upward-downward bending operation knob 4 is in the free state when the movable circular plate 22 exists at the first position. Furthermore, the upward-downward bending operation knob 4 is in the engagement state when the movable circular plate 22 exists at the second position.

The movable circular plate 22 does not rotate around the rotation center axis Ax as described hereinafter and freely moves in the direction along the rotation center axis Ax. Therefore, the first position described hereinbefore and the second position described hereinbefore refer to positions in the direction along the rotation center axis Ax.

The movable circular plate 22 is formed of a circular ring shape as a whole and is formed to have an outer circumferential flange portion 22a, an inward flange 22b, a through-hole 22c, and engagement cam insertion portions 22d.

The outer circumferential flange portion 22a is a part disposed to be fitted to an inner circumferential portion 23c of the friction member 23. Furthermore, the inward flange 22b clamps an inward flange 23b of the friction member 23 with a closed surface 24e of the support member 24.

The through-hole 22c is a through-hole portion formed into an oval shape. The fixing shaft 29 (not illustrated in FIG. 2; see FIG. 3) is inserted in the through-hole 22c. For this reason, the section of the fixing shaft 29 in a predetermined region is formed into an oval shape.

It suffices that the part at which the section is formed into the substantially oval shape in the fixing shaft 29 is only the region in which at least the movable circular plate 22 and the support member 24 are disposed. The section of the other part of the fixing shaft 29, for example, the part around which the click cam plate 27 (described hereinafter) is disposed, is formed into a substantially circular shape as illustrated in FIG. 3.

As described hereinbefore, due to the insertion in the through-hole 22c of the movable circular plate 22 and the forming of the section of the fixing shaft 29 into the substantially oval shape in the region in which the movable circular plate 22 is disposed around the fixing shaft 29, the movable circular plate 22 does not rotate relative to the fixing shaft 29. Simultaneously with this, the movable circular plate 22 freely moves in the direction along the axial direction of the fixing shaft 29, or rotation center axis Ax.

The engagement cam insertion portions 22d are circumferential groove portions in which the engagement cam portions 26a (details will be described hereinafter) of the engagement cam member 26 are inserted. For this purpose, the engagement cam insertion portions 22d are formed into a circular arc shape along the periphery of the rotation center axis Ax. The engagement cam insertion portions 22d are formed in the same number (in the present embodiment, two) as the number (in the present embodiment, two) of engagement cam portions 26a of the engagement cam member 26.

The support member 24 is a support member disposed with the intermediary of a predetermined interval with respect to the movable circular plate 22, or movable member, in the direction along the rotation center axis Ax, or predetermined axis.

The support member 24 is formed to have a cylindrical portion 24b, a through-hole 24c, and engagement cam insertion portions 24d.

The cylindrical portion 24b is formed into a cylindrical shape short in the axial direction as a whole. One surface thereof in the axial direction is opened and the other surface is formed of the closed surface 24e that is substantially closed. The cylindrical portion 24b functions as a housing portion inside which part of the engagement cam member 26 and the click mechanism 105, or click spring 25, click cam plate 27, and so forth thereof, are housed and disposed. The arrangement configuration of the click mechanism 105 inside the cylindrical portion 24b will be described hereinafter (see FIG. 3).

The through-hole 24c is a through-hole portion formed into an oval shape at substantially the central part of the other surface, or closed surface 24e, of the cylindrical portion 24b. In the through-hole 24c, the fixing shaft 29 (not illustrated in FIG. 2; see FIG. 3) whose section also has an oval shape is inserted, similarly to the through-hole 22c of the movable circular plate 22. Due to this, the support member 24 also does not rotate relative to the fixing shaft 29 and simultaneously freely moves in the direction along the axial direction of the fixing shaft 29, or rotation center axis Ax.

The engagement cam insertion portions 24d are circumferential groove portions in which the engagement cam portions 26a (details will be described hereinafter) of the engagement cam member 26 are inserted similarly to the engagement cam insertion portions 22d of the movable circular plate 22. The engagement cam insertion portion 24d is formed into a circular arc shape along the periphery of the rotation center axis Ax in the vicinity of the rim of the through-hole 24c. The engagement cam insertion portions 24d are formed in the same number (in the present embodiment, two) as the number (in the present embodiment, two) of engagement cam portions 26a of the engagement cam member 26.

The friction member 23 is an elastic member disposed between the support member 24 and the movable circular plate 22, or movable member. The friction member 23 is compressed between the support member 24 and the movable circular plate 22 and is deformed when the movable circular plate 22 moves from the first position to the second position. Thereby, the friction member 23 gives a friction force to rotation of the upward-downward bending operation knob 4, or first operation member, and regulates the rotation of the upward-downward bending operation knob 4.

The friction member 23 is a constituent member formed into a circular ring shape. The friction member 23 is disposed coaxially with the rotation center axis Ax in the internal space of the upward-downward bending operation knob 4.

An O-ring (not illustrated) is disposed in an outer circumferential groove portion 23a of the friction member 23. When the friction member 23 is disposed in the internal space of the upward-downward bending operation knob 4, this O-ring (not illustrated) abuts against the inner wall surface of the upward-downward bending operation knob 4 with a predetermined pressing force. Due to this configuration, the configuration is made in such a manner that the friction member 23 rotates together with the upward-downward bending operation knob 4 when the upward-downward bending operation knob 4 is in the free state.

Furthermore, the inward flange 23b is formed at the inner edge portion of a center hole portion 23d of the friction member 23. The inward flange 23b is sandwiched by the movable circular plate 22 and the support member 24 from the upward and downward directions thereof. That is, the movable circular plate 22 and the support member 24 clamp the inward flange 23b of the friction member 23 in the direction along the rotation center axis Ax. Therefore, the friction member 23, the movable circular plate 22, and the support member 24 are all disposed on the same axis of the rotation center axis Ax. The outer circumferential flange portion 22a of the movable circular plate 22 is disposed to be fitted to the inner circumferential portion 23c of the friction member 23.

The engagement cam member 26, or cam member, receives operation input from the external through the engagement lever 5, or second operation member, and rotates around the rotation center axis Ax to move the movable circular plate 22, or movable member, between the first position and the second position.

For this purpose, the engagement cam member 26 is formed to have the engagement cam portions 26a, a support ring portion 26b, and a through-hole 26c as illustrated in FIG. 2 and FIG. 4.

The support ring portion 26b is formed of a flat plate member formed into a circular ring shape. The support ring portion 26b is attached to the click cam plate 27, which is part of the click mechanism 105. The click cam plate 27 is attached to the circular ring portion 5a of the engagement lever 5. Due to this, the engagement cam member 26 is configured integrally with the click cam plate 27 and the engagement lever through the support ring portion 26b. Therefore, the configuration is made in such a manner that, when the engagement lever 5 is rotationally operated, the click cam plate 27 and the engagement cam member 26 rotate in the same direction as the engagement lever 5.

The through-hole 26c is formed at the central part of the support ring portion 26b. The through-hole 26c is a hole in which the fixing shaft 29 is inserted.

The engagement cam portions 26a are multiple arm-shaped portions disposed upright in such a manner as to extend from the outer circumferential edge portion of the support ring portion 26b in the direction parallel to the rotation center axis Ax. The engagement cam portions 26a are formed into a substantially circular cylindrical shape along the periphery of the rotation center axis Ax, or predetermined axis. In the present embodiment, an example in which two engagement cam portions 26a are disposed is illustrated.

The engagement cam portions 26a are constituent members that move the movable circular plate 22, or movable member, between the predetermined first position and the predetermined second position in the direction along the rotation center axis Ax, or predetermined axis.

For this purpose, the engagement cam portions 26a described hereinbefore are formed to have cam surfaces 126 (see FIG. 4; details will be described hereinafter with FIG. 5) made with an inclination with respect to the rotation center axis Ax, or predetermined axis. The cam surface 126 is formed of a curved surface. Furthermore, when the engagement cam member 26 is incorporated into the engagement mechanism 103, part of these cam surfaces 126 always abuts against part of the inward flange 22b of the movable circular plate 22, or movable member.

Due to such a configuration, when the engagement cam member 26 is rotated together with the click cam plate 27 in either the forward or reverse direction around the rotation center axis Ax in response to forward/reverse rotation operation of the engagement lever 5, or second operation member, in a predetermined range around the rotation center axis Ax, the engagement cam member 26 moves the movable circular plate 22 in such a direction as to get closer to the support member 24 or moves the movable circular plate 22 in such a direction as to get further away from the support member 24 in the direction along the rotation center axis Ax. Thereby, the engagement cam member 26 moves the movable circular plate 22 between the first position and the second position to carry out on/off-switching of the engagement state.

Furthermore, when the engagement cam member 26 moves the movable circular plate 22 in such a direction as to get closer to the support member 24 in the direction along the rotation center axis Ax, the friction member 23 is compressed between the movable circular plate 22 and the support member 24. Thereby, the friction member 23 is deformed to extend in the radial direction. Moreover, the compressive force in the direction of the rotation center axis Ax to the friction member 23 between the movable circular plate 22 and the support member 24 is released when the engagement cam member 26 moves the movable circular plate 22 in such a direction as to get further away from the support member 24 in the direction along the rotation center axis Ax. Thereby, the friction member 23 returns to the normal form and the O-ring at the outer circumferential edge portion of the friction member 23 abuts against the inner wall surface of the upward-downward bending operation knob 4 with a predetermined pressing force. In this state, the friction member 23 rotates together with the upward-downward bending operation knob 4. Thus, the rotation of the upward-downward bending operation knob 4 is not inhibited but allowed to freely rotate.

Meanwhile, as described hereinbefore, the engagement cam member 26 described hereinbefore is attached to the click cam plate 27, which is part of the click mechanism 105, through the support ring portion 26b.

Here, the click mechanism 105 is a mechanism unit for giving a predetermined feeling of click to the operator who is operating the engagement lever 5, or second operation member, at the timing when the movable circular plate 22, or movable member, is disposed at either position of the first position or the second position and holding the first position or the second position of the movable circular plate 22 in the direction of the rotation center axis Ax by holding the engagement cam member 26 at the position of this timing.

For this purpose, the click mechanism 105 is configured to have the click spring and the click cam plate 27.

Among them, the click spring 25 is a biasing member and a plate spring member that is disposed along the inner wall surface of the support member 24 and has an elastic force in the radial direction of the support member 24 described hereinbefore. As illustrated in FIG. 3, the click spring 25 is screw-fixed, in a middle part thereof, to the inner wall surface of the support member 24 by screws 25x at multiple places (in the present embodiment, four places). Furthermore, free end portions at both ends of the click spring 25 abut against the outer circumferential edge portion of the click cam plate 27 with a predetermined pressing force due to their own elastic force. At both ends of the click spring 25, multiple click projected portions 25a each oriented in the radial direction are formed.

The click cam plate 27 is a mechanism unit for generating a predetermined feeling of click at a predetermined timing by cooperating with the click spring 25 described hereinbefore when the operator operates the engagement lever 5.

The click cam plate 27 is disposed inside the support member 24 in such a manner as to freely rotate in the same direction as the engagement lever 5 in conjunction with forward/reverse rotation operation of the engagement lever 5 around the rotation center axis Ax.

The click cam plate 27 is formed to have a support portion 27b formed into a flat plate shape, multiple click recessed portions 27a formed at the outer circumferential edge portion of the support portion 27b, and a through-hole 27c pierced at substantially the central part of the support portion 27b.

The support portion 27b has the through-hole 27c at substantially the central part and is attached and supported by the circular ring portion 5a of the engagement lever 5 in the vicinity of the peripheral portion of the through-hole 27c. Due to this, the click cam plate 27 is integrated with the engagement lever 5 and is configured to rotate in the same direction in conjunction with forward/reverse rotation operation of the engagement lever around the rotation center axis Ax.

The multiple click recessed portions 27a are formed at the outer circumferential edge portion of the support portion 27b. These multiple click recessed portions 27a are constituent portions for giving a desired feeling of click to the engagement lever 5 when the multiple click projected portions 25a of the click spring 25 suddenly drop into the click recessed portions 27a.

That is, the multiple click projected portions 25a of the click spring 25 always abut against the outer circumferential edge portion of the click cam plate 27 as described hereinbefore. When the click cam plate 27 rotates in response to rotation operation of the engagement lever 5 described hereinbefore in this state, the multiple click projected portions 25a of the click spring 25 relatively slide along the outer circumferential edge portion of the click cam plate 27 while keeping the state of abutting against this outer circumferential edge portion. At this time, the click projected portion 25a of the click spring 25 drops into one of the multiple click recessed portions 27a at a predetermined timing and gets over it to escape therefrom. When the click projected portion 25a suddenly drops into the click recessed portion 27a in this manner, the desired feeling of click is generated for the engagement lever 5.

The through-hole 27c of the click cam plate 27 is a through-hole in which the rotating shaft 21 and the fixing shaft 29 are inserted.

Next, a more detailed description will be made about the shape of the cam surface 126 of the engagement cam portion 26a of the engagement cam member 26 by mainly using FIG. 5.

As conceptually illustrated in FIG. 5, the cam surface 126 of the engagement cam portion 26a of the engagement cam member 26 is formed to have continuous two inclined surfaces (126a and 126b) and two parallel surfaces (126c and 126d) that are continuous with these two inclined surfaces and are orthogonal to the rotation center axis Ax. In this case, one of the two inclined surfaces will be referred to as the first inclined surface 126a and the other will be referred to as the second inclined surface 126b. Furthermore, one of the two parallel surfaces will be referred to as the first parallel surface 126c and the other will be referred to as the second parallel surface 126d.

The state illustrated in FIG. 5 represents the state in which the movable circular plate 22 exists at the first position. At this time, part of the inward flange 22b of the movable circular plate 22 abuts against the first parallel surface 126c of the cam surface 126 of the engagement cam member 26.

The friction member 23 is disposed between the inward flange 22b of the movable circular plate 22 and the closed surface 24e of the support member 24. However, in FIG. 5, diagrammatic representation of the friction member 23 is omitted.

At the time of this state, the upward-downward bending operation knob 4 is in the free state in which rotation operation around the rotation center axis Ax is not regulated by the engagement mechanism 103. At the time of this state, bending operation is carried out by using the upward-downward bending operation knob 4.

This state, or free state of the engagement mechanism, is held by action of the click mechanism 105, that is, by fixing and keeping the position of the click cam plate 27 integrated with the engagement cam member 26. Therefore, in association with this, the movable circular plate 22 is also held at the first position.

Furthermore, in this state, the engagement lever 5 is operated when the bending operation position based on the upward-downward bending operation knob 4 is desired to be attached.

That is, when the engagement lever 5 is rotationally operated in a predetermined direction, or referred to as engagement direction, around the rotation center axis Ax, the engagement cam member 26 rotates in the same direction simultaneously with this. Suppose that, at this time, in FIG. 5, the engagement cam member 26 rotationally moves in a direction of an arrow R1 in directions along arrows R in FIG. 5, for example.

Along with this, the movable circular plate 22 relatively moves from the first parallel surface 126c to the first inclined surface 126a (what actually rotates is the engagement cam member 26).

Here, a feeling of click is generated due to action of the click mechanism 105 at the point of the transition from the first parallel surface 126c to the first inclined surface 126a (numeral reference P1 in FIG. 5).

Specifically, the click cam plate 27 rotates and the engagement between the click projected portion 25a of the click spring 25 and the click recessed portion 27a of the click cam plate 27 is released. Subsequently to this, the same click projected portion 25a drops into and engages with adjacent another click recessed portion 27a and thereby a feeling of click is generated. This allows the operator to sense that the movable circular plate 22 has moved from the first position and the free state has been canceled and transition to the engagement state, or engagement-on, has been made. The feeling of click at this point is also sensing that the upward-downward bending operation knob 4 has become the free state, or engagement-off, i.e., disposing of the movable circular plate 22 at the first position, at the time of engagement release.

The first inclined surface 126a described hereinbefore is the region to a midway position P2 (see FIG. 5) when the movable circular plate 22 moves from the first position, or engagement-off; free state, to the second position, or engagement-on; engagement state.

Furthermore, the second inclined surface 126b described hereinbefore is an inclined surface continuous with the first inclined surface 126a described hereinbefore and is the region from the midway position P2 described hereinbefore to the second position, or engagement-on.

Moreover, a feeling of click is generated again due to action of the click mechanism 105 at the point of transition of the movable circular plate 22 from the second inclined surface 126b to the second parallel surface 126d (numeral reference P3 in FIG. 5). This allows the operator to sense that the movable circular plate 22 has been disposed at the second position and the upward-downward bending operation knob 4 has become the engagement state, or engagement-on. The feeling of click at this point is also sensing that the engagement state, or engagement-on, has been canceled, or movement of the movable circular plate 22 from the second position, at the time of engagement release.

As described hereinbefore, when the movable circular plate 22 relatively moves in the rotation direction along the first inclined surface 126a and the second inclined surface 126b, the movable circular plate 22 moves in a direction of an arrow X1 in FIG. 5 and moves from the first position toward the second position.

When the movable circular plate 22 relatively moves in the rotation direction along the second inclined surface 126b and the first inclined surface 126a, the movable circular plate 22 moves in a direction of an arrow X2 in FIG. 5 and moves from the second position toward the first position.

Here, directions of arrows X in FIG. 5 are directions along the rotation center axis Ax. Furthermore, the direction of the arrow X1 in FIG. 5 represents the direction in which the movable circular plate 22 gets closer to the support member 24, or direction from the first position toward the second position. Moreover, the direction of the arrow X2 in FIG. 5 represents the direction in which the movable circular plate 22 gets further away from the support member 24, or direction from the second position toward the first position.

In this manner, the movable circular plate 22 moves in the direction along the rotation center axis Ax between the first position and the second position due to the cam surface 126 of the engagement cam member 26.

In this case, when the movable circular plate 22 moves from the first position to the second position, or movement in the direction of the arrow X1 in FIG. 5, the friction member 23 between the movable circular plate 22 and the support member 24 is compressed and deformed to extend in the radial direction. Along with this, the O-ring (not illustrated) at the outer circumferential groove portion 23a of the friction member 23 abuts against the inner wall surface (not illustrated) of the upward-downward bending operation knob 4 with a stronger pressing force. Due to this, rotation of the upward-downward bending operation knob 4 around the rotation center axis Ax is regulated.

As described hereinbefore, the cam surface 126 is formed to have the two inclined surfaces (126a and 126b). In this case, the inclined surfaces are formed in such a manner that the inclination angle of the second inclined surface 126b described hereinbefore is gentle compared with the inclination angle of the first inclined surface 126a described hereinbefore.

By employing such a configuration, the amount of movement of the movable circular plate 22, or movable member, in the direction along the rotation center axis Ax due to the cam surface 126 is changed to become gentler in the middle of compression of the friction member 23 by the movable circular plate 22, i.e., in the middle of the movement of the movable circular plate 22 from the first position to the second position, specifically at the midway position P2 illustrated in FIG. 5.

Here, the first inclined surface 126a is the region closer to the first position. Furthermore, the second inclined surface 126b is the region closer to the second position.

That is, in the bending operation mechanism of the endoscope 1 of the present embodiment, the cam surfaces 126 of the engagement cam portions 26a of the engagement cam member 26 are configured in such a manner that the engagement torque is suddenly displaced with respect to the operation rotation angle of the engagement lever in the first inclined surface 126a formed closer to the first position whereas the engagement torque makes gentler transition with respect to the operation rotation angle of the engagement lever 5 in the second inclined surface 126b formed closer to the second position.

As described hereinbefore, in the bending operation mechanism of the endoscope 1 of the present embodiment, the amount of movement of the movable circular plate 22, or movable member, in the direction along the rotation center axis Ax, or predetermined axis, due to the cam surface 126 is changed to become gentler in the middle of compression of the friction member 23 by the movable circular plate 22, or movable member.

In general, a condition for causing the operator to clearly sense the feeling of click generated due to action of the click mechanism 105 is represented as illustrated next, for example.

Specifically, when the click torque when a feeling of click is generated due to action of the click mechanism 105 is defined as AT and the engagement torque at the timing of the generation of this click is defined as T, it is known that the feeling of click can be sensed more clearly when AT/T is larger.

Therefore, in the case of the operation mechanism including the click mechanism that generates the same feeling of click, there is a tendency that the sensed feeling of click is weakened to a larger extent when the engagement torque at the timing of the generation of the feeling of click is higher.

Furthermore, by increasing the rotation angle of the engagement lever 5 for moving the movable circular plate 22 between the first position and the second position, the increase amount of the engagement torque per unit rotation amount of the engagement lever 5 can be lowered, with the engagement torque kept constant. However, when operability of the operation member is considered, setting the operation rotation angle of the engagement lever 5 needlessly large leads to deterioration of operability and thus the need to set the operation rotation angle of the engagement lever 5 in a predetermined range arises.

Thus, for example, when a configuration is considered in which the displacement of the engagement torque is constant when the movable circular plate 22 that moves in the direction along the rotation center axis Ax due to action of the engagement cam member 26 moves between the first position and the second position, a configuration is conceivable in which the cam surface is formed of one inclined surface having a constant inclination as illustrated by a two-dot chain line [B1] in FIG. 5. When the configuration is made as hereinbefore, the engagement torque is displaced as illustrated by a two-dot chain line [B2] in FIG. 5. In this case, the displacement of the engagement torque makes constant transition. Furthermore, at this time, the engagement torque when the movable circular plate 22 is disposed at the second position is illustrated by T2.

On the other hand, the displacement of the engagement torque in the configuration of the present embodiment, i.e., in the case in which the cam surface 126 is formed of the two inclined surfaces (126a and 126b) as illustrated by a solid line [A1] in FIG. 5, is as follows. Specifically, as described hereinbefore and as illustrated by a solid line [A2] in FIG. 5, the engagement torque is suddenly displaced with respect to the operation rotation angle of the operation member in the first inclined surface 126a closer to the first position, and the engagement torque makes gentler transition with respect to the operation rotation angle of the same operation member in the second inclined surface 126b formed closer to the second position. Furthermore, at this time, the engagement torque when the movable circular plate 22 is disposed at the second position is illustrated by T1.

Due to this configuration, the amount of rotational force of the engagement lever at the point of transition of the movable circular plate 22 from the second inclined surface 126b to the second parallel surface 126d (numeral reference P3 in FIG. 5), i.e., at the timing when the movable circular plate 22 is disposed at the second position, can be set smaller. Therefore, the feeling of click generated at this timing is easier to sense.

Although the upward-downward direction bending operation mechanism 101 is described in detail thus far, the left-right direction bending operation mechanism 102 has substantially the same configuration as the upward-downward direction bending operation mechanism 101 described hereinbefore and operation thereof is also substantially the same. Therefore, regarding the left-right direction bending operation mechanism 102, merely the configuration thereof will be simply described hereinafter.

As illustrated in FIG. 6, the left-right direction bending operation mechanism 102 is composed mainly of the left-right bending operation knob 6, a left-right bending operation knob lower cover 6a, a rotating shaft 31, the engagement knob 7, an engagement mechanism 104, and so forth.

The engagement mechanism 104 is composed mainly of a movable circular plate 32, a friction member 33, a support member 34, an engagement cam member 36, an engagement fixing shaft 38, a click mechanism 106 including a click spring 35, a click cam plate 37, and so forth.

The left-right direction bending operation mechanism 102 in the present embodiment is basically formed of substantially the same configuration as the upward-downward direction bending operation mechanism 101 described hereinbefore. In this case, the left-right direction bending operation mechanism 102 (see FIG. 6) is different in that the engagement knob 7 is disposed instead of the engagement lever 5 in the upward-downward direction bending operation mechanism 101 (see FIG. 2).

Furthermore, the respective constituent members of the upward-downward direction bending operation mechanism 101 described hereinbefore basically employ a configuration in which they are lined up and disposed in the direction along the rotation center axis Ax. Similarly to this, the respective constituent members of the left-right direction bending operation mechanism 102 are also lined up and disposed in the direction along the rotation center axis Ax. However, the left-right direction bending operation mechanism 102 is different in that the respective constituent members of the left-right direction bending operation mechanism 102 are arranged in reverse order with respect to the arrangement of the respective constituent members of the upward-downward direction bending operation mechanism 101 described hereinbefore.

Therefore, in the following description about the configuration of the left-right direction bending operation mechanism 102, the member with the same name is given a numeral reference obtained by adding 10 to the numeral reference in FIG. 2. In addition, detailed description of individual members is omitted based on the premise that they can implement the same operation although the shape is somewhat different.

The left-right bending operation knob 6 is an operation member of a rotation system with which an operator carries out rotation operation when bending operation in the left-right direction is carried out.

The left-right bending operation knob lower cover 6a is a cover member that covers the lower surface side of the left-right bending operation knob 6. Furthermore, the respective constituent parts of the left-right direction bending operation mechanism 102 including the engagement mechanism 104 are disposed in a space formed between the left-right bending operation knob 6 and the left-right bending operation knob lower cover 6a.

The rotating shaft 31 is a power transmitting member for transmitting rotation of the left-right bending operation knob 6 to a sprocket or pulley, or part of the left-right direction bending operation mechanism 102, that is not illustrated in the diagram and rotating the sprocket or pulley.

An engaging portion 31a formed at one end of the rotating shaft 31 engages with multiple engaged projected portions 6b formed around the rotation center axis Ax (see one-dot chain line in FIG. 6) in the left-right bending operation knob lower cover 6a. Due to this, when the left-right bending operation knob 6 is rotated around the rotation center axis Ax together with the left-right bending operation knob lower cover 6a, the rotating shaft 31 also rotates in the same direction in conjunction with the left-right bending operation knob 6.

Meanwhile, the other end 31b of the rotating shaft 31 penetrates the left-right bending operation knob lower cover 6a and the outer wall surface of the operation portion 3 and is disposed to protrude in the internal space thereof. The rotating shaft 31 is disposed to be inserted in the rotating shaft 21 described hereinbefore and freely rotate inside it. Furthermore, the rotating shaft 31 penetrates the left-right bending operation knob lower cover 6a and is disposed to protrude to the inside of the operation portion 3.

The engagement knob 7 is an operation member that acts on the engagement mechanism 104. That is, the engagement knob 7 is an operation member for switching operation between an engagement state, or engagement-on, in which the rotation position of the left-right bending operation knob 6 is attached and the desired bending angle of the bending portion 12 in the left-right direction is kept and a free state, or engagement-off, in which bending operation can be freely carried out through canceling of the fixed-kept state of this engagement state, or engagement-on.

As the engagement knob 7 in the present embodiment, an operation member of a rotation system is exemplified. The engagement knob 7 is disposed freely rotatably around the rotation center axis Ax of the left-right bending operation knob 6. This allows the operator to carry out on/off-switching of the engagement state of the left-right bending operation knob 6, i.e., switch the engagement state and the free state, by rotating the engagement knob 7 around the rotation center axis Ax of the left-right bending operation knob 6.

The engagement knob 7 is disposed freely rotatably relative to a fixing shaft (not illustrated) that protrudes from the operation portion 3. An engaging portion of the click cam plate 37 (described hereinafter), which is part of the click mechanism 106 to be described hereinafter, engages with the inside surface of the engagement knob 7 and thereby the click cam plate 37 is integrally disposed. Furthermore, the engagement cam member 36 (described hereinafter) is integrally attached to the click cam plate 37 by a screw or the like. Due to this, the click cam plate 37 and the engagement cam member 36 are configured to rotate in the same direction in conjunction with rotation operation of the engagement knob 7.

The engagement mechanism 104 is a mechanism portion that receives operation input of the engagement knob 7 and implements the engagement state and the free state of the left-right bending operation knob 6.

Among the constituent members of the engagement mechanism 104, the movable circular plate 32 is formed to have an outer circumferential flange portion 32a, an inward flange 32b, a through-hole 32c, and engagement cam insertion portions 32d. The shape and operation of each part of the movable circular plate 32 are substantially the same as the movable circular plate 22 described hereinbefore.

Similarly to the movable circular plate 22 described hereinbefore, the movable circular plate 32 is disposed inside the left-right bending operation knob 6, or first operation member. The movable circular plate 32 is a movable member that receives action of engagement cam portions 36a of the engagement cam member 36 and can move between a position, or referred to as first position, at which the movable circular plate 32 permits rotation of the left-right bending operation knob 6, or first operation member, and a position, or referred to as second position, at which the movable circular plate 32 regulates rotation of the left-right bending operation knob 6, or first operation member, through separation from this first position in the direction along the rotation center axis Ax, or predetermined axis. Here, the left-right bending operation knob 6 is in the free state when the movable circular plate 32 exists at the first position. Furthermore, the left-right bending operation knob 6 is in the engagement state when the movable circular plate 32 exists at the second position.

The support member 34 in the constituent members of the engagement mechanism 104 is formed to have a cylindrical portion 34b, a through-hole 34c, and engagement cam insertion portions 34d. The shape and operation of each part of the support member 34 are substantially the same as the support member 24 described hereinbefore.

The support member 34 is a support member disposed with the intermediary of a predetermined interval with respect to the movable circular plate 32, or movable member, in the direction along the rotation center axis Ax, or predetermined axis.

The friction member 33 in the constituent members of the engagement mechanism 104 is formed to have an outer circumferential groove portion 33a, an inward flange 33b, an inner circumferential portion (not illustrated), and a center hole portion 33d. The shape and operation of each part of the friction member 33 are substantially the same as the friction member 23 described hereinbefore.

The friction member 33 is an elastic member disposed between the support member 34 and the movable circular plate 32, or movable member. The friction member 33 is compressed between the support member 34 and the movable circular plate 32 and is deformed when the movable circular plate 32 moves from the first position to the second position. Thereby, the friction member 33 gives a friction force to rotation of the left-right bending operation knob 6, or first operation member, and regulates the rotation of the left-right bending operation knob 6.

The engagement fixing shaft 38 in the constituent members of the engagement mechanism 104 is a shaft member that causes the movable circular plate 32 and the support member 34 not to rotate and allows the movable circular plate 32 to freely move in the direction along the axial direction of the engagement fixing shaft 38, or rotation center axis Ax, in the internal space of the left-right bending operation knob 6. For this purpose, the engagement fixing shaft 38 is attached in such a manner that the axial center corresponds with the direction along the rotation center axis Ax in the internal space of the left-right bending operation knob 6. Furthermore, the section of an intermediate part of the engagement fixing shaft 38 is formed into a substantially oval shape. Moreover, in conformity to this, the through-hole 32c of the movable circular plate 32 and the through-hole 34c of the support member 34 are formed into a similar oval shape. In addition, the engagement fixing shaft 38 is inserted in the respective through-holes 32c and 34c of the movable circular plate 32 and the support member 34.

Furthermore, the engagement fixing shaft 38 is inserted also in a through-hole 36c of the engagement cam member 36 and a through-hole 37c of the click cam plate 37. At this time, the section of the part inserted in the respective through-holes 36c and 37c of the engagement cam member 36 and the click cam plate 37 in the engagement fixing shaft 38 is formed into a substantially circular shape. Due to this, with respect to the engagement fixing shaft 38, the engagement cam member 36 and the click cam plate 37 are disposed freely rotatably around the fixing shaft 38, or around the rotation center axis Ax. In addition, the engagement cam member 36 is attached to be integrated with the click cam plate 37 as described hereinbefore.

Moreover, the engagement cam member 36, or cam member, receives operation input from the external through the engagement knob 7, or second operation member, or operation input by forward/reverse rotation operation of the engagement knob 7 in a predetermined range around the rotation center axis Ax, and rotates around the rotation center axis Ax together with the click cam plate 37. Thereby, the engagement cam member 36 moves the movable circular plate 32, or movable member, between the first position and the second position and carries out on/off-switching of the engagement state of the left-right bending operation knob 6, or first operation member.

For this purpose, as illustrated in FIG. 6 and FIG. 7, the engagement cam member 36 is formed to have the engagement cam portions 36a, a support ring portion 36b, and the through-hole 36c. The shape and operation of each part of the engagement cam member 36 are substantially the same as the engagement cam member 26 described hereinbefore.

Therefore, the configuration is made in such a manner that, when forward/reverse rotation operation of the engagement knob 7 is carried out in the predetermined range, the click cam plate 37 and the engagement cam member 36 rotate in the same direction as the engagement knob 7.

The engagement cam portions 36a are constituent members that move the movable circular plate 32, or movable member, between the predetermined first position and the predetermined second position in the direction along the rotation center axis Ax, or predetermined axis.

For this purpose, the engagement cam portions 36a described hereinbefore are formed to have cam surfaces 136 (see FIG. 7) made with an inclination with respect to the rotation center axis Ax, or predetermined axis. Also regarding these engagement cam portions 36a, the shape and operation thereof are the same as the engagement cam portions 26a described hereinbefore (see also FIG. 5).

Meanwhile, as described hereinbefore, the engagement cam member 36 described hereinbefore is attached to the click cam plate 37, which is part of the click mechanism 106, through the support ring portion 36b.

Here, the click mechanism 106 is a mechanism unit for giving a predetermined feeling of click to the operator who is operating the engagement knob 7, or second operation member, at the timing when the movable circular plate 32, or movable member, is disposed at either position of the first position or the second position and holding the position of the engagement cam member 36 at the first position or the second position.

For this purpose, the click mechanism 106 is configured to have the click spring and the click cam plate 37. Among them, the shape and operation of the click spring are the same as the click spring 25 described hereinbefore. Furthermore, the basic configuration and operation of the click cam plate 37 are the same as the click cam plate 27 described hereinbefore although the shape is slightly different. Specifically, the click cam plate 37 is formed to have a support portion 37b formed into a flat plate shape, multiple click recessed portions 37a formed at the outer circumferential edge portion of the support portion 37b, a through-hole 37c pierced at substantially the central part of the support portion 37b, and an engaging portion 37d that engages with an engaged portion on the inside surface of the engagement knob 7.

In order to bend the bending portion 12 of the insertion portion 2 of the endoscope 1 in the upward-downward direction by using the operation mechanism of the endoscope in the present embodiment configured in this manner, or bending operation mechanism 100 included in the endoscope 1, the upward-downward bending operation knob 4 is rotationally operated in a desired direction. Furthermore, the left-right bending operation knob 6 is rotationally operated in a desired direction in order to bend the bending portion 12 in the left-right direction. Thereby, the bending portion 12 is bent in the upward-downward or left-right direction to be set to a desired bent state.

In general, the bending portion 12 of the insertion portion 2 of the endoscope 1 has resilience to the straight line shape along the insertion axis direction. Therefore, when the respective bending operation knobs 4 and 6 are operated to set the bending portion 12 to a bent state, the bending portion 12 returns to the straight line shape if the application of the amount of bending operation force is not continued.

Thus, conventionally in the bending operation mechanism of the general endoscope, an engagement mechanism for fixing and keeping the bent state by bending operation of each bending operation knob is disposed and operation members such as engagement lever and engagement knob are disposed for engagement operation thereof.

In the case of keeping the desired bent state of the bending portion 12 in the endoscope 1, for example, in the case of keeping the bent state in the upward-downward direction, the engagement lever 5 is operated while bending operation by the upward-downward bending operation knob 4 is carried out. Furthermore, in the case of keeping the bent state in the left-right direction, the engagement knob 7 is operated while bending operation by the left-right bending operation knob 6 is carried out.

When bending operation is carried out by using the upward-downward bending operation knob 4, the upward-downward bending operation knob 4 is set to the free state, or engagement-off state, by the engagement mechanism 103. At this time, the movable circular plate 22 of the engagement mechanism 103 exists at the first position.

Furthermore, when bending operation is carried out by using the left-right bending operation knob 6, the left-right bending operation knob 6 is set to the free state, or engagement-off state, by the engagement mechanism 104. At this time, the movable circular plate 32 of the engagement mechanism 104 exists at the first position.

In this state, the engagement lever 5 and the engagement knob 7 are rotationally operated around the rotation center axis Ax in a predetermined direction, i.e., in such a direction as to set each of the respective bending operation knobs 4 and 6 to the engagement state. Thereby, the engagement cam members 26 and 36 rotate around the rotation center axis Ax and the movable circular plates 22 and 32 move from the first position to the second position in the direction along the rotation center axis Ax. Along with this, the respective movable circular plates 22 and 32 compress the respective friction members 23 and 33 and deform them in the radial direction. Thereby, the respective friction members 23 and 33 carry out rotation regulation of the respective bending operation knobs 4 and 6.

At this time, when the respective movable circular plates 22 and 32 move from the first position to the second position, the displacement of the engagement torque becomes gentler at a midway position (see numeral reference P2 in FIG. 5) due to action of the two inclined surfaces 126a and 126b of the cam surface 126. Then, at the timing when the respective movable circular plates 22 and 32 are disposed at the second position, the click mechanisms 105 and 106 act and a predetermined feeling of click is generated. This causes the respective bending operation knobs 4 and 6 to become the predetermined engagement state in which rotation regulation is carried out.

To cancel this engagement state, the engagement lever 5 and the engagement knob 7 are rotationally operated around the rotation center axis Ax in a predetermined direction, i.e., in such a direction as to cancel the engagement state of each of the respective bending operation knobs 4 and 6, or such a direction as to make the free state. In the following, by similar (however, in reverse order of the order described hereinbefore) action, the engagement cam members 26 and 36 are rotated around the rotation center axis Ax and the respective movable circular plates 22 and 32 are moved from the second position to the first position in the direction along the rotation center axis Ax. Then, at the timing when the respective movable circular plates 22 and 32 are disposed at the first position, the click mechanisms 105 and 106 act and a predetermined feeling of click is generated. Due to this, rotation regulation of the respective bending operation knobs 4 and 6 is released and the bending operation knobs 4 and 6 become the predetermined free state in which free rotation is allowed.

As described hereinbefore, according to the first embodiment described hereinbefore, the configuration is made in such a manner that the movable circular plates 22 and 32 are moved between the first position and the second position in the direction along the rotation center axis Ax due to rotation action of the engagement cam members 26 and 36 and on/off-switching of the engagement state of the respective bending operation knobs 4 and 6 is carried out. In this case, in the engagement cam members 26 and 36 for moving the movable circular plates 22 and 32 in the direction along the rotation center axis Ax, the cam surfaces 126 and 136 of the engagement cam portions 26a and 36a are formed of the two inclined surfaces (126a and 126b (136a and 136b)).

By employing such a configuration, according to the present embodiment, the displacement of the engagement torque when the movable circular plates 22 and 32 that move in the direction along the rotation center axis Ax due to action of the engagement cam members 26 and 36 move between the first position and the second position can be made gentler at the midway position.

Therefore, according to this, the engagement torque at the timing when the movable circular plates 22 and 32 are disposed at the second position can be made lower without changing the rotation range of the engagement operation members 5 and 7. Accordingly, the feeling of click generated at this second position can be made easier to sense.

Moreover, by employing such a configuration, even when a configuration in which the engagement holding force is further enhanced is made, a clear feeling of click can be always obtained and thus the operator is allowed to sense on/off-switching of the engagement state more easily. From this, this configuration can contribute to improvement in the feeling of use of the endoscope including this operation mechanism of an endoscope.

Second Embodiment

Next, an operation mechanism of an endoscope in a second embodiment of the disclosed technology will be described hereinafter.

The basic configuration of the present embodiment is substantially the same as the first embodiment described hereinbefore. Therefore, the same configuration as the first embodiment described hereinbefore is given the same numeral reference and description thereof is omitted, and only the different part will be described in detail hereinafter.

Figure 8:
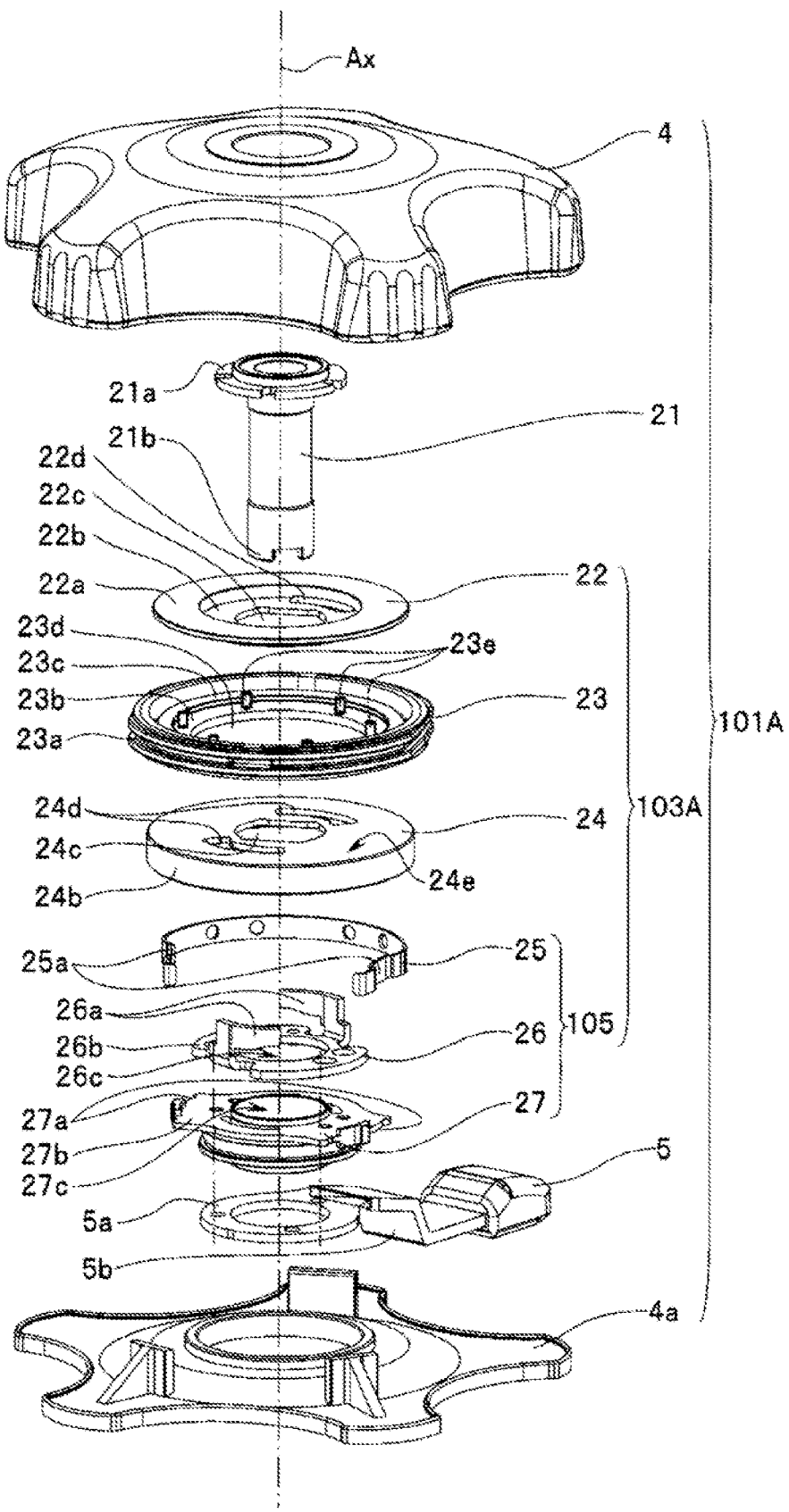
FIG. 8 is a main-part enlarged exploded perspective view illustrating the configuration of an upward-downward direction bending operation mechanism in an operation mechanism of an endoscope in a second embodiment of the disclosed technology.
Figure 9:
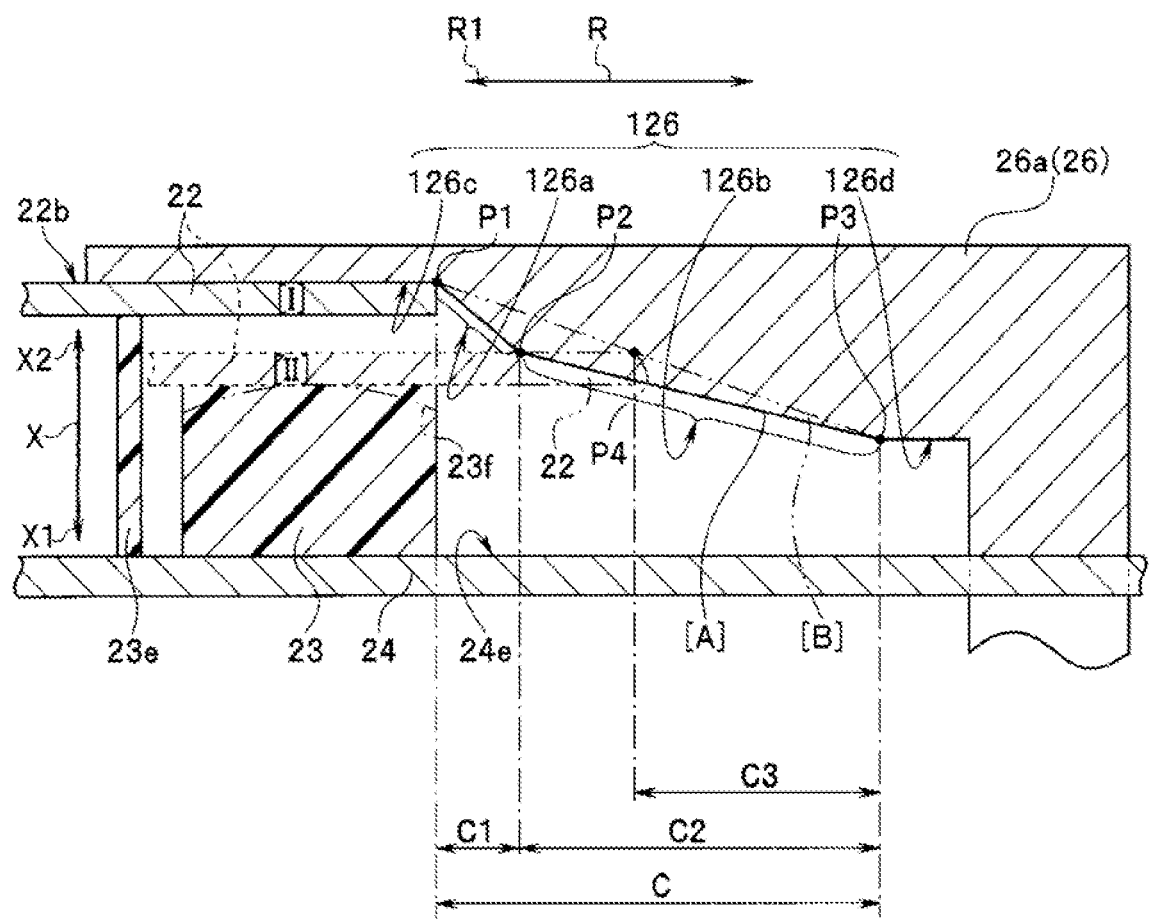
FIG. 9 is a conceptual diagram that conceptually illustrates an engagement mechanism in the upward-downward direction bending operation mechanism in FIG. 8 and illustrates the shape of a cam surface of an engagement cam member by a section.
Figure 10:
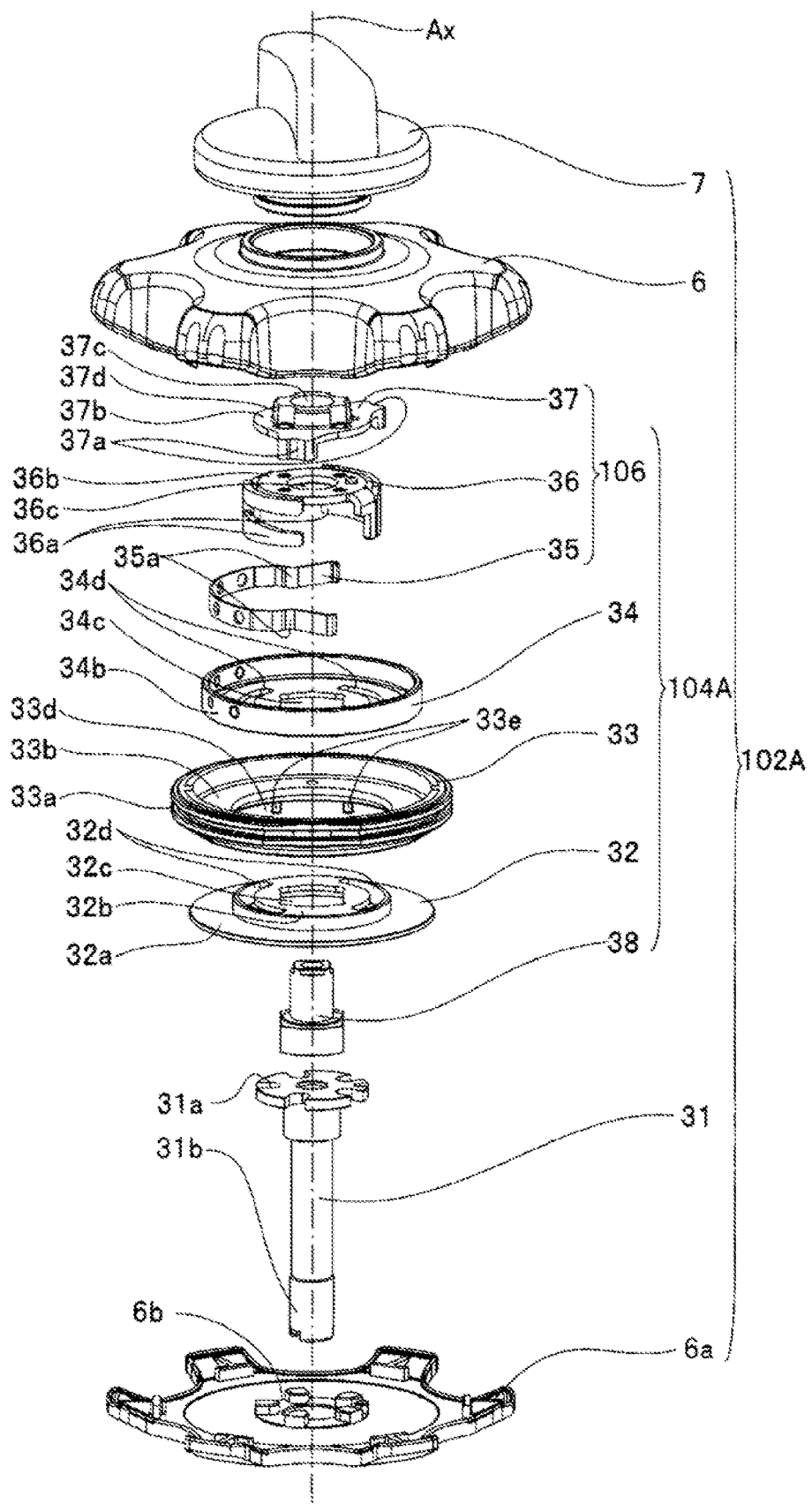
FIG. 10 is a main-part enlarged exploded perspective view illustrating the configuration of a left-right direction bending operation mechanism in the operation mechanism of an endoscope in the second embodiment of the disclosed technology.

FIG. 8 to FIG. 10 are diagrams illustrating the second embodiment of the disclosed technology. Among them, FIG. 8 is a main-part enlarged exploded perspective view illustrating the configuration of an upward-downward direction bending operation mechanism in the operation mechanism of an endoscope in the second embodiment of the disclosed technology. FIG. 9 is a conceptual diagram that conceptually illustrates an engagement mechanism in the upward-downward direction bending operation mechanism illustrated in FIG. 8 and illustrates the shape of a cam surface of an engagement cam member by a section. FIG. 10 is a main-part enlarged exploded perspective view illustrating the configuration of a left-right direction bending operation mechanism in the operation mechanism of an endoscope in the second embodiment of the disclosed technology.

The overall configuration of an endoscope including the operation mechanism of an endoscope in the second embodiment of the disclosed technology is substantially the same as the first embodiment described hereinbefore. Therefore, regarding the overall configuration of the endoscope, reference to FIG. 1 is made and description thereof is omitted.

Next, the bending operation mechanism 100 that is the operation mechanism of an endoscope in the present embodiment and is included in the endoscope 1 will be described hereinafter by using FIG. 8 to FIG. 10, FIG. 3, FIG. 4, and FIG. 7.

The bending operation mechanism 100 of the endoscope 1 (see FIG. 1) in the present embodiment is composed of an upward-downward direction bending operation mechanism 101A (see FIG. 8) for bending the bending portion 12 of the insertion portion 2 of the endoscope 1 in the upward-downward direction and a left-right direction bending operation mechanism 102A (see FIG. 10) for bending the bending portion 12 in the left-right direction.

The upward-downward direction bending operation mechanism 101A (see FIG. 8) and the left-right direction bending operation mechanism 102A (see FIG. 10) are basically formed of the same configuration as the first embodiment described hereinbefore. Therefore, only the different part will be described in detail in the following explanation.

In the present embodiment, an engagement mechanism 103A of the upward-downward direction bending operation mechanism 101A (see FIG. 8) is composed mainly of the movable circular plate 22, the friction member 23, elastic bodies 23e for repulsion of the movable circular plate, the support member 24, the engagement cam member 26, the click mechanism 105 including the click spring 25, the click cam plate 27, and so forth.

The multiple elastic bodies 23e for repulsion of the movable circular plate (details will be described hereinafter) intervene between the movable circular plate 22 and the friction member 23. This suppresses the occurrence of the situation in which one surface, or surface opposed to the inward flange 23b of the friction member 23, of the inward flange 22b of the movable circular plate 22 gets tight contact with and adsorbs one surface, or surface opposed to the inward flange 22b of the movable circular plate 22, of the inward flange 23b of the friction member 23.

Furthermore, the elastic bodies 23e described hereinbefore for repulsion of the movable circular plate play a role in, when the upward-downward bending operation knob 4 is in the free state, reducing a friction load generated by the friction member 23 that rotates together with the upward-downward bending operation knob 4 described hereinbefore and the movable circular plate 22 that does not rotate relative to the upward-downward bending operation knob 4 and reducing the rotation torque of the upward-downward bending operation knob 4.

On the one surface, or surface opposed to the inward flange 22b of the movable circular plate 22, of the inward flange 23b, the multiple elastic bodies 23e for repulsion of the movable circular plate are disposed to protrude in such a manner as to extend in the direction parallel to the rotation center axis Ax. These elastic bodies 23e for repulsion of the movable circular plate are formed into a circular column shape with a small diameter by a material having elasticity.

By intervening between the movable circular plate 22 and the friction member 23, the elastic bodies 23e for repulsion of the movable circular plate are disposed for reducing the contact area between both so as to prevent the movable circular plate 22 and the friction member 23 from getting tight contact with each other. That is, the elastic bodies 23e for repulsion of the movable circular plate are biasing members that bias the movable circular plate 22, or movable member, toward the first position.

Due to the disposing of these elastic bodies 23e for repulsion of the movable circular plate, these elastic bodies 23e for repulsion of the movable circular plate play a role in reducing the friction load generated by the friction member 23 that rotates together with the upward-downward bending operation knob 4 and the movable circular plate 22 that does not rotate relative to the upward-downward bending operation knob 4 and reducing the rotation torque of the upward-downward bending operation knob 4 when the upward-downward bending operation knob 4 is rotationally operated when the engagement state of the upward-downward bending operation knob 4 is in the off-state, or free state.

That is, even when being in contact with the movable circular plate 22, the elastic bodies 23e for repulsion of the movable circular plate generate only extremely-low friction resistance. Therefore, the elastic bodies 23e for repulsion of the movable circular plate are configured in such a manner as to hardly affect the rotation torque of the upward-downward bending operation knob 4 at the time of engagement-off and be capable of ensuring smooth rotation operation at the time of engagement-off.

Next, a detailed description will be made about the shape of the cam surface 126 of the engagement cam portion 26a of the engagement cam member 26 by mainly using FIG. 9.

As conceptually illustrated in FIG. 9, the cam surface 126 of the engagement cam portion 26a of the engagement cam member 26 is formed to have the continuous two inclined surfaces (126a and 126b) and the two parallel surfaces (126c and 126d) that are continuous with these two inclined surfaces and are orthogonal to the rotation center axis Ax. In this case, one of the two inclined surfaces will be referred to as the first inclined surface 126a and the other will be referred to as the second inclined surface 126b. Furthermore, one of the two parallel surfaces will be referred to as the first parallel surface 126c and the other will be referred to as the second parallel surface 126d.

The state illustrated in FIG. 9 represents the state in which the movable circular plate 22 exists at the first position (solid line of numeral reference 22 in FIG. 9; state of numeral reference [I]) and the timing when the movable circular plate 22 starts compression of the friction member 23 through execution of engagement operation (dotted line of numeral reference 22 in FIG. 9; state of numeral reference [II]). When the movable circular plate 22 exists at the first position (a solid line of numeral reference 22 in FIG. 9), one surface of the inward flange 22b of the movable circular plate 22 abuts against the first parallel surface 126c of the cam surface 126 of the engagement cam member 26. Furthermore, at this time, the other surface of the inward flange 22b abuts against the multiple elastic bodies 23e for repulsion of the movable circular plate.

Thereby, the contact of the movable circular plate 22 with the friction member 23 is suppressed. Therefore, at this time, a slight gap exists between the movable circular plate 22 and the friction member 23 and both are not in direct contact.

At the time of this state, the upward-downward bending operation knob 4 is in the free state in which rotation operation around the rotation center axis Ax is not regulated by the engagement mechanism 103A. That is, this state is the state in which bending operation can be carried out by using the upward-downward bending operation knob 4.

This state, or free state of the engagement mechanism, is held by action of the click mechanism 105, that is, by fixing and keeping the position of the click cam plate 27 integrated with the engagement cam member 26. Therefore, the movable circular plate 22 is also held at the first position in association with this.

Furthermore, in this state, the engagement lever 5 is operated when the bending operation position by the upward-downward bending operation knob 4 is desired to be attached.

That is, when the engagement lever 5 is rotationally operated in a predetermined direction, or referred to as engagement direction, around the rotation center axis Ax, the engagement cam member 26 rotates in the same direction simultaneously with this. Suppose that, at this time, in FIG. 9, the engagement cam member 26 rotationally moves in the direction of the arrow R1 in the directions along the arrows R in FIG. 9, for example.

Along with this, the movable circular plate 22 relatively moves from the first parallel surface 126c to the first inclined surface 126a (what actually rotates is the engagement cam member 26).

Here, a feeling of click is generated due to action of the click mechanism 105 at the point of the transition from the first parallel surface 126c to the first inclined surface 126a (numeral reference P1 in FIG. 9).

Specifically, the click cam plate 27 rotates and the engagement between the click projected portion 25a of the click spring 25 and the click recessed portion 27a of the click cam plate 27 is released. Subsequently to this, the same click projected portion 25a drops into and engages with adjacent another click recessed portion 27a and thereby a feeling of click is generated. This allows the operator to sense that the movable circular plate 22 has moved from the first position and the free state has been canceled and transition to the engagement state, or engagement-on, has been made. The feeling of click at this point is also sensing that the upward-downward bending operation knob 4 has become the free state, or engagement-off, i.e., disposing of the movable circular plate 22 at the first position, at the time of engagement release.

The first inclined surface 126a described hereinbefore is the region to a midway position P2 (see FIG. 9) when the movable circular plate 22 moves from the first position, or engagement-off; free state, to the second position, or engagement-on; engagement state.

In this region, the movable circular plate 22 relatively moves from the position illustrated by the solid line of numeral reference 22 in FIG. 9 to the position illustrated by the dotted line of numeral reference 22 in FIG. 9. At this time, the movable circular plate 22 moves in a direction along arrows X parallel to the rotation center axis Ax and in a direction of an arrow X1 while compressing and deforming the elastic body 23e for repulsion of the movable circular plate. Then, when the movable circular plate 22 reaches the midway position P2 (see FIG. 9) described hereinbefore, the other surface of the movable circular plate 22 abuts against the friction member 23.

When the engagement cam member 26 further rotationally moves in the direction of the arrow R1 in FIG. 9 from the state in which the movable circular plate 22 exists at the midway position P2 (see FIG. 9), the movable circular plate 22 moves in the direction of the arrow X1 in FIG. 9 while compressing and deforming the elastic body 23e for repulsion of the movable circular plate and the friction member 23. At this time, the movable circular plate 22 relatively moves along the cam surface of the second inclined surface 126b (what actually rotates is the engagement cam member 26).

Moreover, a feeling of click is generated again due to action of the click mechanism 105 at the point of transition of the movable circular plate 22 from the second inclined surface 126b to the second parallel surface 126d (numeral reference P3 in FIG. 9). This allows the operator to sense that the movable circular plate 22 has been disposed at the second position and the upward-downward bending operation knob 4 has become the engagement state, or engagement-on. The feeling of click at this point is also sensing that the engagement state, or engagement-on, has been canceled, or movement of the movable circular plate 22 from the second position, at the time of engagement release.

As described hereinbefore, when the movable circular plate 22 relatively moves along the first inclined surface 126a and the second inclined surface 126b, the movable circular plate 22 moves in the direction of the arrow X1 in FIG. 9 and moves from the first position toward the second position.

When the movable circular plate 22 relatively moves along the second inclined surface 126b and the first inclined surface 126a, the movable circular plate 22 moves in a direction of an arrow X2 in FIG. 9 and moves from the second position toward the first position.

Here, the directions of the arrows X in FIG. 9 are directions along the rotation center axis Ax. Furthermore, the direction of the arrow X1 in FIG. 9 represents the direction in which the movable circular plate 22 gets closer to the support member 24, or direction from the first position toward the second position. Moreover, the direction of the arrow X2 in FIG. 9 represents the direction in which the movable circular plate 22 gets further away from the support member 24, or direction from the second position toward the first position.

In this manner, the movable circular plate 22 moves in the direction along the rotation center axis Ax between the first position and the second position due to the cam surface 126 of the engagement cam member 26.

In this case, when the movable circular plate 22 moves from the first position to the second position, or movement in the direction of the arrow X1 in FIG. 9, the friction member 23 between the movable circular plate 22 and the support member 24 is compressed and deformed to extend in the radial direction. Along with this, the O-ring (not illustrated) at the outer circumferential groove portion 23a of the friction member 23 abuts against the inner wall surface (not illustrated) of the upward-downward bending operation knob 4 with a stronger pressing force. Due to this, rotation of the upward-downward bending operation knob 4 around the rotation center axis Ax is regulated.

As described hereinbefore, the cam surface 126 is formed to have the two inclined surfaces (126a and 126b). In this case, the inclined surfaces are formed in such a manner that the inclination angle of the second inclined surface 126b described hereinbefore is gentle compared with the inclination angle of the first inclined surface 126a described hereinbefore.

By employing such a configuration, the amount of movement of the movable circular plate 22, or movable member, in the direction along the rotation center axis Ax due to the cam surface 126 is changed to become gentler after the movable circular plate 22 starts the compression of the friction member 23, i.e., after the movable circular plate 22 abuts against the friction member 23 in the middle of the movement of the movable circular plate 22 from the first position to the second position, specifically after the movable circular plate 22 passes through the midway position P2 illustrated in FIG. 9.

Here, supposing that the rotation angle of the engagement cam member 26, or engagement operation member 5 or 7, is defined in a predetermined range, the region in which the inclination is set in the cam surface is a region represented by numeral reference C illustrated in FIG. 9, for example.

In the bending operation mechanism of an endoscope in the present embodiment, as described hereinbefore, two inclined surfaces are formed (see numeral reference [A] of the cam surface illustrated by a solid line in FIG. 9) in the region in which the inclination of the cam surface 126 is set (region in the range illustrated by numeral reference C in FIG. 9). In this case, the first inclined surface 126a is the region closer to the first position (region in a range illustrated by numeral reference C1 in FIG. 9) and the second inclined surface 126b is a region closer to the second position (region in a range illustrated by numeral reference C2 in FIG. 9). Furthermore, among them, the region in which the movable circular plate 22 compresses and deforms the friction member 23 to generate engagement torque is the region of the second inclined surface 126b (numeral reference C2 in FIG. 9).

On the other hand, conventionally in the bending operation mechanism of the general endoscope, supposing that the cam surface is formed of one inclined surface, for example, the cam surface becomes what is illustrated by a two-dot chain line in FIG. 9 (numeral reference [B] in FIG. 9) in this case.

In such a conventional configuration, when the engagement cam member 26 rotates and the movable circular plate 22 moves in the direction of the arrow X1, the compression of the friction member 23 is started when the movable circular plate 22 reaches a predetermined position P4 in this FIG. 9 (a two-dot chain line in FIG. 9). Therefore, the necessary engagement torque has to be given in the region from the timing P4 when the compression of the friction member 23 is started to the point P3 at which the movable circular plate 22 is disposed at the second position (region in the range illustrated by numeral reference C3 in FIG. 9). In this case, the inclination of the cam surface after the compression of the friction member 23 is started becomes sharp and the amount of operation force also becomes large.

In contrast, in the bending operation mechanism of the endoscope 1 in the present embodiment, in the cam surface 126 of the engagement cam portions 26a of the engagement cam member 26, the first inclined surface 126a formed closer to the first position is set as the region in which engagement torque has not yet been applied although rotation operation of the engagement lever 5 is carried out. In this region, the inclination of the cam surface is set to a steep inclination so that the movable circular plate 22 can ensure a predetermined movement amount with a small rotation angle. On the other hand, the configuration is made in such a manner that the engagement torque makes gentler transition with respect to the operation rotation angle of the engagement lever 5 in the second inclined surface 126b formed closer to the second position.

As described hereinbefore, in the bending operation mechanism of the endoscope 1 of the present embodiment, the amount of movement of the movable circular plate 22, or movable member, in the direction along the rotation center axis Ax, or predetermined axis, due to the cam surface 126 is changed to become gentler after the movable circular plate 22, or movable member, has started the compression of the friction member 23.

Due to this, according to the configuration of the present embodiment, without setting the rotation angle of the engagement cam member 26, or engagement operation member 5 or 7, the engagement torque can be made gentler while the rotation angle in the predetermined range is kept, and thus operability of engagement operation is not impaired.

Although the upward-downward direction bending operation mechanism 101A is described in detail thus far, the left-right direction bending operation mechanism 102A has substantially the same configuration as the upward-downward direction bending operation mechanism 101A described hereinbefore and operation thereof is also substantially the same.

Furthermore, the relationship between the configuration of the upward-downward direction bending operation mechanism 101A (FIG. 8) and the configuration of the left-right direction bending operation mechanism 102A (FIG. 10) in the present embodiment is substantially the same as the relationship between the configuration of the upward-downward direction bending operation mechanism 101 (FIG. 2) and the left-right direction bending operation mechanism 102 (FIG. 6) in the first embodiment described hereinbefore. Therefore, regarding the left-right direction bending operation mechanism 102A in the present embodiment, merely the configuration thereof will be simply described hereinafter.

The engagement mechanism 104A of the left-right direction bending operation mechanism 102A (see FIG. 10) in the present embodiment is composed mainly of the movable circular plate 32, the friction member 33, elastic bodies 33e for repulsion of the movable circular plate, the support member 34, the engagement cam member 36, the engagement fixing shaft 38, the click mechanism 106 including the click spring 35, the click cam plate 37, and so forth.

The left-right direction bending operation mechanism 102A in the present embodiment is basically formed of substantially the same configuration as the upward-downward direction bending operation mechanism 101A described hereinbefore. In this case, the left-right direction bending operation mechanism 102A (see FIG. 10) is different in that the engagement knob 7 is disposed instead of the engagement lever 5 in the upward-downward direction bending operation mechanism 101A (see FIG. 8).

Furthermore, the respective constituent members of the upward-downward direction bending operation mechanism 101A described hereinbefore basically employ a configuration in which they are lined up and disposed in the direction along the rotation center axis Ax. Similarly to this, the respective constituent members of the left-right direction bending operation mechanism 102A are also lined up and disposed in the direction along the rotation center axis Ax. However, the left-right direction bending operation mechanism 102A is different in that the respective constituent members of the left-right direction bending operation mechanism 102A are arranged in reverse order with respect to the arrangement of the respective constituent members of the upward-downward direction bending operation mechanism 101A described hereinbefore.

The multiple elastic bodies 33e for repulsion of the movable circular plate intervene between the movable circular plate 32 and the friction member 33. These elastic bodies 33e for repulsion of the movable circular plate suppress the occurrence of the situation in which one surface of the movable circular plate 32 gets tight contact with and adsorbs one surface of the friction member 33. Thereby, when the left-right bending operation knob 6 is in the free state, the elastic bodies 33e for repulsion of the movable circular plate reduce a friction load generated by the friction member 33 that rotates together with the left-right bending operation knob 6 and the movable circular plate 32 that does not rotate relative to the left-right bending operation knob 6 and reduce the rotation torque of the left-right bending operation knob 6. The other configuration is substantially the same as the upward-downward direction bending operation mechanism 101A. As described hereinbefore, according to the second embodiment described hereinbefore, the configuration is made in such a manner that the movable circular plates 22 and 32 are moved between the first position and the second position in the direction along the rotation center axis Ax due to rotation action of the engagement cam members 26 and 36 and on/off-switching of the engagement state of the respective bending operation knobs 4 and 6 is carried out similarly to the first embodiment described hereinbefore. In this case, in the engagement cam members 26 and 36 for moving the movable circular plates 22 and 32 in the direction along the rotation center axis Ax, the cam surfaces 126 and 136 of the engagement cam portions 26a and 36a are formed of the two inclined surfaces (126a and 126b (136a and 136b)).

Moreover, in the present embodiment, furthermore in the first inclined surface 126a (136a), the cam surface is formed with a steep inclination as the region in which only the elastic bodies 23e or 33e for repulsion of the movable circular plate are compressed. In addition, in the second inclined surface 126b (136b) after the movable circular plate 22 or 32 has started the compression of the friction member 23 or 33, the cam surface is formed to be gentler.

By employing such a configuration, according to the present embodiment, the same effects as the first embodiment described hereinbefore can be obtained. In addition, further reduction in the rotation operation torque can be implemented.

In order to further smooth and stabilize rotation operability of the respective bending operation knobs 4 and 6 at the time of engagement-off, for example, a configuration may be employed in which a lubricant or the like for enhancing slidability is applied between the movable circular plates 22 and 32 and the friction members 23 and 33.

As described hereinbefore, in the present embodiment, reduction in the rotation operation torque of the respective bending operation knobs 4 and 6 at the time of engagement-off, or at the time of free state, is intended by making the elastic bodies 23e and 33e for repulsion of the movable circular plate intervene between the movable circular plates 22 and 32 and the friction members 23 and 33.

In this case, if the elastic force, or repellent force, by the elastic bodies 23e and 33e for repulsion of the movable circular plate is small, when the engagement mechanism is switched from the engagement-on state to the free state, an adsorptive force by the lubricant described hereinbefore or the like acts, which possibly makes the state in which the movable circular plates 22 and 32 stick to the friction members 23 and 33. In such a state, even when the respective bending operation knobs 4 and 6 are in the free state in which bending operation is possible, a friction load is generated between the movable circular plates 22 and 32 and the friction members 23 and 33, so that the rotation operation torque of the respective bending operation knobs 4 and 6 increases.

Thus, in view of this, it is desirable to employ a shape with which air enters between both members, or sliding surface, easily and adsorption with the movable circular plates 22 and 32 does not occur as shape contrivance of the contact surface, or sliding surface, of the friction members 23 and 33 to the movable circular plates 22 and 32. Specifically, for example, it suffices that the sectional shape of the contact surface of the friction members 23 and 33 with the movable circular plates 22 and 32 is configured in such a manner that the section has a rounded shape as illustrated by a two-dot chain line (numeral reference 23f) in FIG. 9.

If such a configuration is employed, even when the elastic force, or repellent force, of the elastic bodies 23e and 33e for repulsion of the movable circular plate is small, adsorption between the movable circular plates 22 and 32 and the friction members 23 and 33 can be suppressed and operability of the respective bending operation knobs 4 and 6 at the time of engagement-off, or at the time of free state, can be made always smooth and stable.

It is obvious that the disclosed technology is not limited to the embodiments described hereinbefore and various modifications and applications can be carried out in such a range as not to depart from the gist of the invention. Furthermore, inventions at various stages are included in the embodiments described hereinbefore and various inventions can be extracted based on appropriate combinations in multiple constituent requirements that are disclosed. For example, if the problems to be solved by the invention can be solved and effects of the invention are obtained even when several constituent requirements are deleted from all constituent requirements illustrated in one embodiment described hereinbefore, the configuration from which these constituent requirements are deleted can be extracted as an invention. Moreover, constituent elements across different embodiments may be combined as appropriate. This invention is not restricted by a specific embodiment thereof except that the invention is limited by the accompanying claims.

The disclosed technology can be applied to not only an endoscope control apparatus in the medical field but also an endoscope control apparatus in the industrial field.

In sum, one aspect of the disclosed technology is directed to an endoscope having respective first and second operations, a movable member, respective support and friction members, a cam member and a click mechanism all of which are engaged with one another to operate the endoscope during an operation. A first operation member is disposed in the endoscope and is rotationally operated around a predetermined axis to carry out operation of the endoscope. A second operation member is disposed in the endoscope and is rotationally operated around the predetermined axis to carry out rotation regulation of the first operation member. A movable member is disposed inside the first operation member and is movable between a first position at which the movable member permits rotation of the first operation member and a second position at which the movable member regulates rotation of the first operation member through separation from the first position in a direction along the predetermined axis. A support member is disposed with intermediary of a predetermined interval with respect to the movable member in the direction along the predetermined axis. A friction member that is disposed between the support member and the movable member and is compressed and deformed between the support member and the movable member when the movable member moves from the first position to the second position so as to give a friction force to the rotation of the first operation member and to regulate the rotation of the first operation member. A cam member having a cam surface that is made with an inclination with respect to the predetermined axis and abuts against part of the movable member. The cam member receives operation input from external through the second operation member and moves the movable member between the first position and the second position. A click mechanism holds the cam member at the first position or the second position in which an amount of movement of the movable member in the direction along the predetermined axis by the cam surface changes to become gentler in middle of compression of the friction member by the movable member.

The first operation member is a rotation knob for causing a bending portion in the endoscope to act. The cam member is formed into a circular cylindrical shape along periphery of the predetermined axis. The cam surface of the cam member has two inclined surfaces. The cam surface of the cam member is formed of a curved surface.

Another aspect of the disclosed technology is directed to an endoscope having an endoscope having respective first and second operations, a movable member, respective support and friction members, a cam member and a biasing member all of which engaged with one another to operate the endoscope during an operation. A first operation member is disposed in the endoscope and is rotationally operated around a predetermined axis to carry out operation of the endoscope. A second operation member that is disposed in the endoscope and is rotationally operated around the predetermined axis to carry out rotation regulation of the first operation member. A movable member is disposed inside the first operation member and is movable between a first position at which the movable member permits rotation of the first operation member and a second position at which the movable member regulates rotation of the first operation member through separation from the first position in a direction along the predetermined axis. A support member is disposed with intermediary of a predetermined interval with respect to the movable member in the direction along the predetermined axis. A friction member is disposed between the support member and the movable member and is compressed and deformed between the support member and the movable member when the movable member moves from the first position to the second position so as to give a friction force to the rotation of the first operation member and to regulate the rotation of the first operation member. A cam member having a cam surface is made with an inclination with respect to the predetermined axis and abuts against part of the movable member. The cam member receives operation input from external through the second operation member and moves the movable member between the first position and the second position. A biasing member that biases the movable member toward the first position in which an amount of movement of the movable member in the direction along the predetermined axis by the cam surface changes to become gentler after the movable member has started compression of the friction member.

The first operation member is a rotation knob for causing a bending portion to act in the endoscope. The cam member is formed into a circular cylindrical shape along periphery of the predetermined axis. The cam surface of the cam member has two inclined surfaces. The cam surface of the cam member is formed of a curved surface.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future. The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An endoscope, comprising:
   a first operation knob being disposed in the endoscope and being rotationally operated around a predetermined axis to carry out operation of the endoscope;
   a second operation knob being disposed in the endoscope and being rotationally operated around the predetermined axis to carry out rotation regulation of the first operation knob;
   a movable plate being disposed inside the first operation knob and being movable between a first position at which the movable plate permits rotation of the first operation knob and a second position at which the movable plate regulates rotation of the first operation knob through separation from the first position in a direction along the predetermined axis;
   a support plate disposed with intermediary of a predetermined interval with respect to the movable plate in the direction along the predetermined axis;
   an elastic member that is disposed between the support plate and the movable plate and being compressed and deformed between the support plate and the movable plate when the movable plate moves from the first position to the second position so as to give a friction force to the rotation of the first operation knob and to regulate the rotation of the first operation knob;
   a cam member having a cam surface that includes a first inclined surface and a second inclined surface with respect to the predetermined axis, the cam surface abutting against part of the movable plate, and the cam member receiving operation input from external through the second operation knob and moving the movable plate between the first position and the second position; and
   a click mechanism that includes a click spring and a click cam plate holds the cam member at the first position or the second position, wherein a first torque displacement with respect to a first rotation angle of the second operation knob on the first inclined surface is larger than a second torque displacement with respect to a second rotation angle of the second operation knob on the second inclined surface.

2. The endoscope of claim 1, wherein the first operation knob is a rotation knob for causing a bending portion in the endoscope to act.

3. The endoscope of claim 1, wherein the cam member is formed into a circular cylindrical shape along periphery of the predetermined axis.

4. The endoscope of claim 1, wherein the cam surface of the cam member has two inclined surfaces.

5. The endoscope of claim 1, wherein the cam surface of the cam member is formed of a curved surface.

6. An endoscope, comprising:
a first operation knob being disposed in the endoscope and being rotationally operated around a predetermined axis to carry out operation of the endoscope;
a second operation knob that being disposed in the endoscope and being rotationally operated around the predetermined axis to carry out rotation regulation of the first operation knob;
a movable plate being disposed inside the first operation knob and being movable between a first position at which the movable plate permits rotation of the first operation knob and a second position at which the movable plate regulates rotation of the first operation knob through separation from the first position in a direction along the predetermined axis;
a support plate disposed with intermediary of a predetermined interval with respect to the movable plate in the direction along the predetermined axis;
a friction member being disposed between the support plate and the movable plate and being compressed and deformed between the support plate and the movable plate when the movable plate moves from the first position to the second position so as to give a friction force to the rotation of the first operation knob and to regulate the rotation of the first operation knob;
a cam member having a cam surface that includes a first inclined surface and a second inclined surface with respect to the predetermined axis, the cam member abutting against part of the movable plate, and the cam member receiving operation input from external through the second operation knob and moves the movable plate between the first position and the second position; and
a biasing member that biases the movable plate toward the first position wherein a first torque displacement with respect to a first rotation angle of the second operation knob on the first inclined surface is larger than a second torque displacement with respect to a second rotation angle of the second operation knob on the second inclined surface.

7. The endoscope of claim 6, wherein the first operation knob is a rotation knob for causing a bending portion to act in the endoscope.

8. The endoscope of claim 6, wherein the cam member is formed into a circular cylindrical shape along periphery of the predetermined axis.

9. The endoscope of claim 8, wherein the cam surface of the cam member has two inclined surfaces.

10. The endoscope of claim 8, wherein the cam surface of the cam member is formed of a curved surface.

* * * * *